US012186509B2

(12) United States Patent
Fischell et al.

(10) Patent No.: US 12,186,509 B2
(45) Date of Patent: *Jan. 7, 2025

(54) INTRAVASCULAR DELIVERY SYSTEM AND METHOD FOR PERCUTANEOUS CORONARY INTERVENTION

(71) Applicant: VANTIS VASCULAR, INC., Kalamazoo, MI (US)

(72) Inventors: Tim A. Fischell, Kalamazoo, MI (US); Frank S. Saltiel, Willowbrook, IL (US)

(73) Assignee: VANTIS VASCULAR, INC., Kalamazoo, MI (US)

( * ) Notice: Subject to any disclaimer, the term of this patent is extended or adjusted under 35 U.S.C. 154(b) by 34 days.

This patent is subject to a terminal disclaimer.

(21) Appl. No.: 18/191,400

(22) Filed: Mar. 28, 2023

(65) Prior Publication Data

US 2023/0293861 A1 Sep. 21, 2023

Related U.S. Application Data

(63) Continuation of application No. 16/793,120, filed on Feb. 18, 2020, now Pat. No. 11,642,500, which is a (Continued)

(51) Int. Cl.
*A61M 25/10* (2013.01)
*A61M 25/00* (2006.01)
(Continued)

(52) U.S. Cl.
CPC ........ *A61M 25/104* (2013.01); *A61M 25/005* (2013.01); *A61M 25/008* (2013.01);
(Continued)

(58) Field of Classification Search
CPC ............ A61M 25/104; A61M 25/0905; A61M 25/0169; A61M 25/0054; A61M 25/0068;
(Continued)

(56) References Cited

U.S. PATENT DOCUMENTS 3,388,703 A 6/1968 Bowes
3,633,579 A 1/1972 Alley et al.
(Continued)

FOREIGN PATENT DOCUMENTS

JP H11-347131 12/1999
WO WO 2019/164592 8/2019
(Continued)

OTHER PUBLICATIONS

U.S. Appl. No. 16/184,706 filed filed Nov. 8, 2018, Root et al.
(Continued)

*Primary Examiner* — Emily L Schmidt
*Assistant Examiner* — Antarius S Daniel
(74) *Attorney, Agent, or Firm* — Knobbe, Martens, Olson & Bear, LLP

(57) ABSTRACT

The subject guide catheter extension/pre-dilatation system includes an outer delivery sheath, an inner member extending within the sheath, and a mechanism for engagement/disengagement of the inner member to/from the sheath. The inner member is configured with a tapered distal tip having a delivery micro-catheter and a pre-dilatation balloon member attached to the tapered distal tip in proximity to the micro-catheter. The outer delivery sheath and the inner member are modified for different engagement/disengagement mechanisms operation. The delivery micro-catheter provides for an improved crossability for the balloon member to the treatment site in an atraumatic, expedited and convenient fashion. During the cardiac procedure, a guidewire and a guide catheter are advanced to the vicinity of the treatment site within a blood vessel. Subsequent thereto, the inner member and outer delivery sheath, in their engaged configuration, are advanced along the guidewire inside the guide catheter towards the site of treatment. Once at the treatment site, the balloon member is inflated for (Continued)

pre-dilatation treatment. Subsequently, the inner member is disengaged and retracted from the outer delivery sheath, and a stent is delivered to the treatment site inside the outer delivery sheath.

20 Claims, 30 Drawing Sheets

Related U.S. Application Data continuation-in-part of application No. 16/132,878, filed on Sep. 17, 2018, which is a continuation-in-part of application No. 15/899,603, filed on Feb. 20, 2018, now Pat. No. 11,491,313.

(51) Int. Cl.
  *A61M 25/01* (2006.01)
  *A61M 25/09* (2006.01)

(52) U.S. Cl.
  CPC . *A61M 25/0102* (2013.01); *A61M 2025/0081* (2013.01); *A61M 25/09* (2013.01); *A61M 2025/1079* (2013.01); *A61M 2025/1081* (2013.01); *A61M 2205/0266* (2013.01); *A61M 2205/6081* (2013.01); *A61M 2210/12* (2013.01)

(58) Field of Classification Search
  CPC .......... A61M 25/0108; A61M 25/0023; A61M 25/0012; A61M 25/008; A61M 25/0136; A61M 25/10; A61M 2025/0046; A61M 2025/0042; A61M 2025/0062; A61M 2025/0183; A61M 2025/0175; A61M 2025/1079; A61M 2025/1081; A61M 2025/0024; A61M 2025/0004; A61M 2025/0006; A61F 2/958; A61F 2/966
  See application file for complete search history.

(56) References Cited

U.S. PATENT DOCUMENTS

| | | | |
|---|---|---|---|
| 5,102,390 A | 4/1992 | Crittenden et al. | |
| 5,234,416 A | 8/1993 | Macaulay et al. | |
| 5,425,723 A | 6/1995 | Wang | |
| 5,704,926 A | 1/1998 | Sutton | |
| 5,769,819 A | 6/1998 | Schwab et al. | |
| 5,813,405 A * | 9/1998 | Montano, Jr. ...... | A61M 25/0905 |
| | | | 600/585 |
| 5,947,925 A | 9/1999 | Ashiya et al. | |
| 6,120,480 A | 9/2000 | Zhang et al. | |
| 6,179,813 B1 * | 1/2001 | Ballow ............. | A61M 25/0054 |
| | | | 604/173 |
| 6,585,747 B1 | 7/2003 | Limon et al. | |
| 6,648,854 B1 | 11/2003 | Patterson et al. | |
| 7,993,351 B2 | 8/2011 | Worley et al. | |
| 8,048,032 B2 | 11/2011 | Root et al. | |
| 8,142,413 B2 | 3/2012 | Root et al. | |
| 8,292,850 B2 | 10/2012 | Root et al. | |
| 8,361,057 B2 | 1/2013 | Tanghoej et al. | |
| 8,365,087 B2 | 1/2013 | Glaser-Seidnitzer et al. | |
| 8,652,193 B2 | 2/2014 | Dorn | |
| 8,747,428 B2 | 6/2014 | Fischell et al. | |
| 8,821,485 B2 | 9/2014 | Herberer | |
| RE45,380 E | 2/2015 | Root et al. | |
| 8,996,095 B2 | 3/2015 | Anderson et al. | |
| 8,996,096 B2 | 3/2015 | Kinsley et al. | |
| RE45,760 E | 10/2015 | Root et al. | |
| RE45,776 E | 10/2015 | Root et al. | |
| RE46,116 E | 8/2016 | Root et al. | |
| 9,681,882 B2 | 6/2017 | Garrison et al. | |
| 9,687,634 B2 | 6/2017 | Grovender et al. | |
| 9,764,118 B2 | 9/2017 | Anderson et al. | |
| RE47,379 E | 5/2019 | Root et al. | |
| 10,449,339 B2 | 10/2019 | Wilson et al. | |
| 10,786,655 B2 | 9/2020 | Lenker | |
| 11,020,133 B2 * | 6/2021 | Wilson ............. | A61B 17/12109 |
| 11,065,019 B1 | 7/2021 | Chou et al. | |
| 11,224,450 B2 | 1/2022 | Chou et al. | |
| 11,399,852 B2 | 8/2022 | Wilson et al. | |
| 11,491,313 B2 | 11/2022 | Fischell et al. | |
| 11,576,691 B2 | 2/2023 | Chou et al. | |
| 11,642,500 B2 | 5/2023 | Fischell et al. | |
| 11,712,266 B2 | 8/2023 | Fischell et al. | |
| 11,903,613 B2 | 2/2024 | Fischell et al. | |
| 11,998,236 B2 | 6/2024 | Fischell et al. | |
| 2002/0087076 A1 | 7/2002 | Meguro et al. | |
| 2002/0183826 A1 | 12/2002 | Dorn et al. | |
| 2003/0097094 A1 | 5/2003 | Ouriel et al. | |
| 2003/0105451 A1 | 6/2003 | Westlund et al. | |
| 2003/0153925 A1 | 8/2003 | Breskot et al. | |
| 2004/0098020 A1 | 5/2004 | Nardeo | |
| 2005/0182387 A1 | 8/2005 | Webler | |
| 2005/0273074 A1 | 12/2005 | Lewis | |
| 2006/0033334 A1 | 2/2006 | Weber et al. | |
| 2008/0183128 A1 | 7/2008 | Morriss et al. | |
| 2008/0281228 A1 | 11/2008 | Parodi et al. | |
| 2009/0018525 A1 | 1/2009 | Waite et al. | |
| 2009/0082800 A1 | 3/2009 | Janardhan | |
| 2009/0156953 A1 | 6/2009 | Wondka et al. | |
| 2010/0082000 A1 | 4/2010 | Honeck et al. | |
| 2010/0305475 A1 | 12/2010 | Hinchliffe et al. | |
| 2011/0054503 A1 | 3/2011 | Rizk et al. | |
| 2011/0112567 A1 | 5/2011 | Lenker et al. | |
| 2011/0301502 A1 | 12/2011 | Gill | |
| 2012/0065590 A1 | 3/2012 | Bierman et al. | |
| 2012/0078096 A1 | 3/2012 | Krolik et al. | |
| 2013/0116701 A1 | 5/2013 | Wang et al. | |
| 2013/0237962 A1 | 9/2013 | Kawai | |
| 2014/0012281 A1 | 1/2014 | Wang et al. | |
| 2014/0018773 A1 | 1/2014 | Wang et al. | |
| 2014/0058251 A1 | 2/2014 | Stigall et al. | |
| 2014/0194918 A1 | 7/2014 | Tegels | |
| 2014/0236088 A1 | 8/2014 | Al-Rashdan et al. | |
| 2014/0276618 A1 | 9/2014 | Di Caprio et al. | |
| 2015/0005801 A1 | 1/2015 | Marquis et al. | |
| 2015/0151090 A1 | 6/2015 | Sutton et al. | |
| 2015/0173782 A1 | 6/2015 | Garrison et al. | |
| 2015/0265806 A1 | 9/2015 | Kawaguchi | |
| 2016/0121080 A1 * | 5/2016 | Cottone ............ | A61M 25/0069 |
| | | | 604/528 |
| 2016/0144155 A1 | 5/2016 | Simpson et al. | |
| 2016/0249942 A1 | 9/2016 | Olson | |
| 2016/0346506 A1 | 12/2016 | Jackson et al. | |
| 2017/0028170 A1 | 2/2017 | Ho | |
| 2018/0008801 A1 | 1/2018 | Solar et al. | |
| 2018/0126121 A1 | 5/2018 | Mauch | |
| 2018/0193042 A1 | 7/2018 | Wilson et al. | |
| 2018/0344493 A1 | 12/2018 | Epstein | |
| 2019/0015631 A1 | 1/2019 | Comerota et al. | |
| 2019/0255297 A1 | 8/2019 | Fischell et al. | |
| 2019/0255299 A1 | 8/2019 | Fischell et al. | |
| 2020/0179661 A1 | 6/2020 | Fischell et al. | |
| 2021/0212707 A1 | 7/2021 | Chou et al. | |
| 2021/0259718 A1 | 8/2021 | Wilson et al. | |
| 2021/0338256 A1 | 11/2021 | Chou et al. | |
| 2022/0047285 A1 | 2/2022 | Chou et al. | |
| 2022/0175401 A1 | 6/2022 | Wilson et al. | |
| 2022/0313292 A1 | 10/2022 | Wilson et al. | |
| 2022/0338888 A1 | 10/2022 | Chou et al. | |
| 2022/0370761 A1 | 11/2022 | Chou et al. | |
| 2022/0409239 A1 | 12/2022 | Fischell et al. | |
| 2023/0122087 A1 | 4/2023 | Fischell et al. | |
| 2023/0404620 A1 | 12/2023 | Fischell et al. | |

(56) References Cited

U.S. PATENT DOCUMENTS

2024/0123187 A1    4/2024   Fischell et al.
2024/0138877 A1    5/2024   Fischell et al.

FOREIGN PATENT DOCUMENTS

WO    WO 2021/167653     8/2021
WO    WO 2022/271999    12/2022
WO    WO 2024/081328     4/2024

OTHER PUBLICATIONS

U.S. Appl. No. 16/220,925 filed filed Nov. 12, 2018, Root et al.
U.S. Appl. No. 16/220,951 filed filed Dec. 14, 2018, Root et al.
U.S. Appl. No. 16/220,975 filed filed Dec. 14, 2018, Root et al.
U.S. Appl. No. 16/220,996 filed filed Dec. 14, 2018, Root et al.
Biometrics, "What are Micro-Catheters?", Sep. 15, 2015.
International Search Report and written Opinion of International Searching Authority (US) Regarding Corresponding Application PCT/US2019/012678, Dated Mar. 25, 2019.
International Search Report and Written Opinion of PCT Application No. PCT/US2020/057064, dated Jan. 25, 2021; 26 pages.
International Search Report and Written Opinion of PCT Application No. PCT/US2022/034800, dated Sep. 23, 2022; 15 pages.
Extended European Search Report for EP Application No. 20919805.0, dated Feb. 16, 2024; 9 pages.
International Search Report and Written Opinion of PCT Application No. PCT/US2023/034964, dated Jan. 23, 2024; 12 pages.

\* cited by examiner

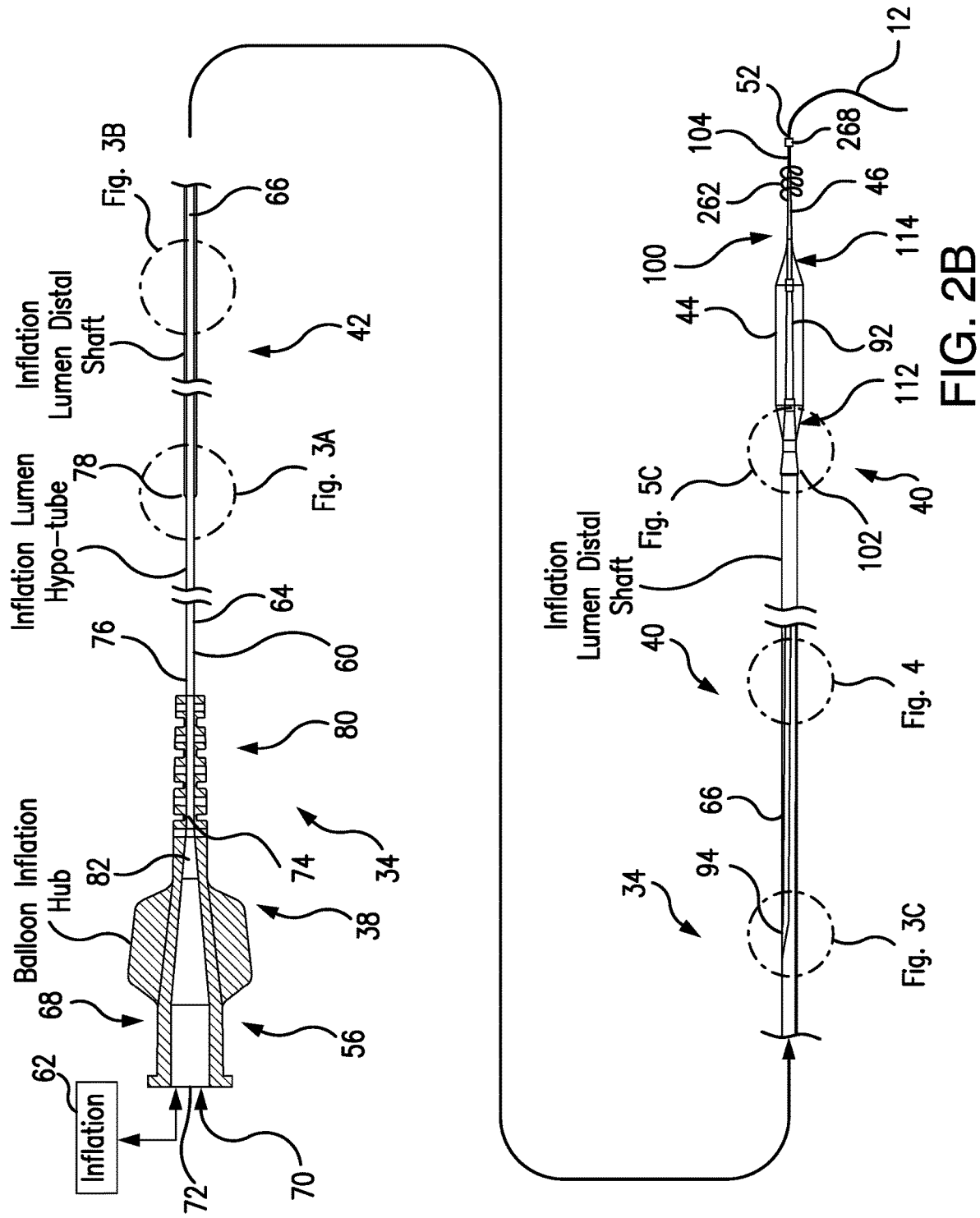

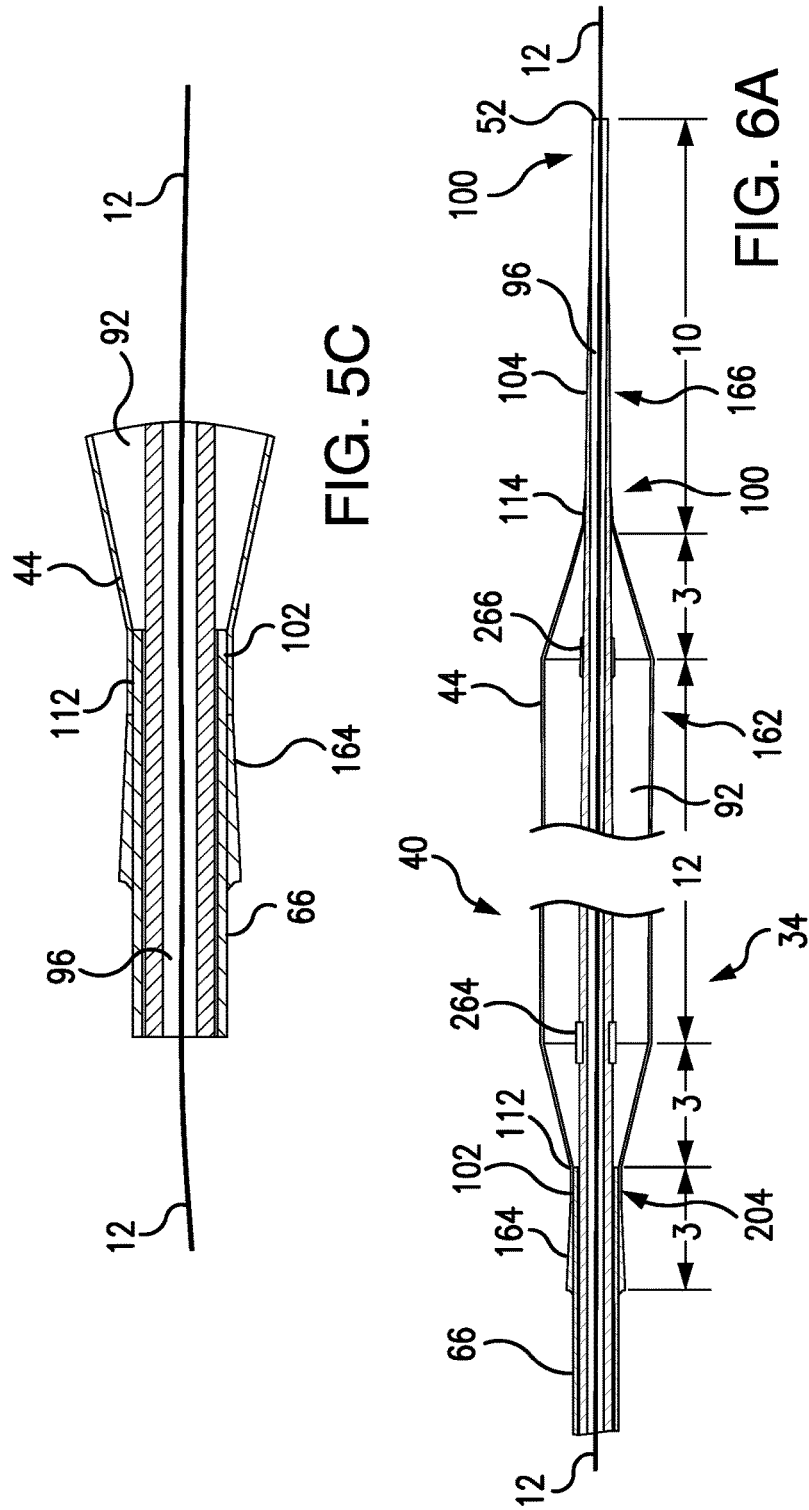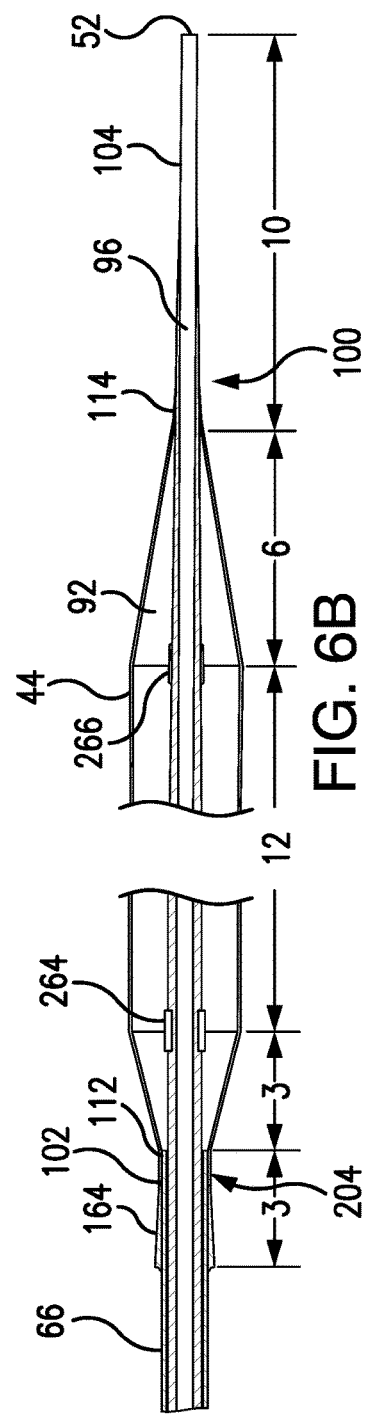

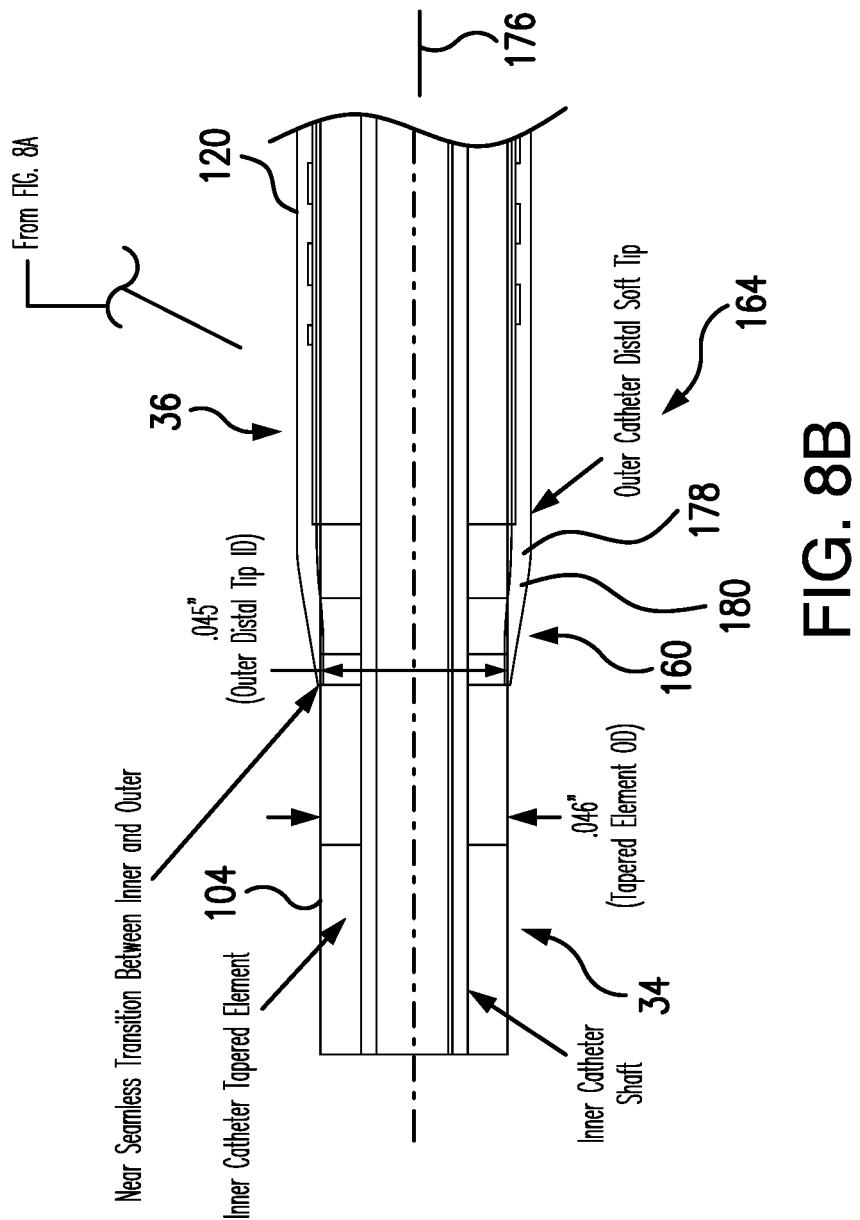

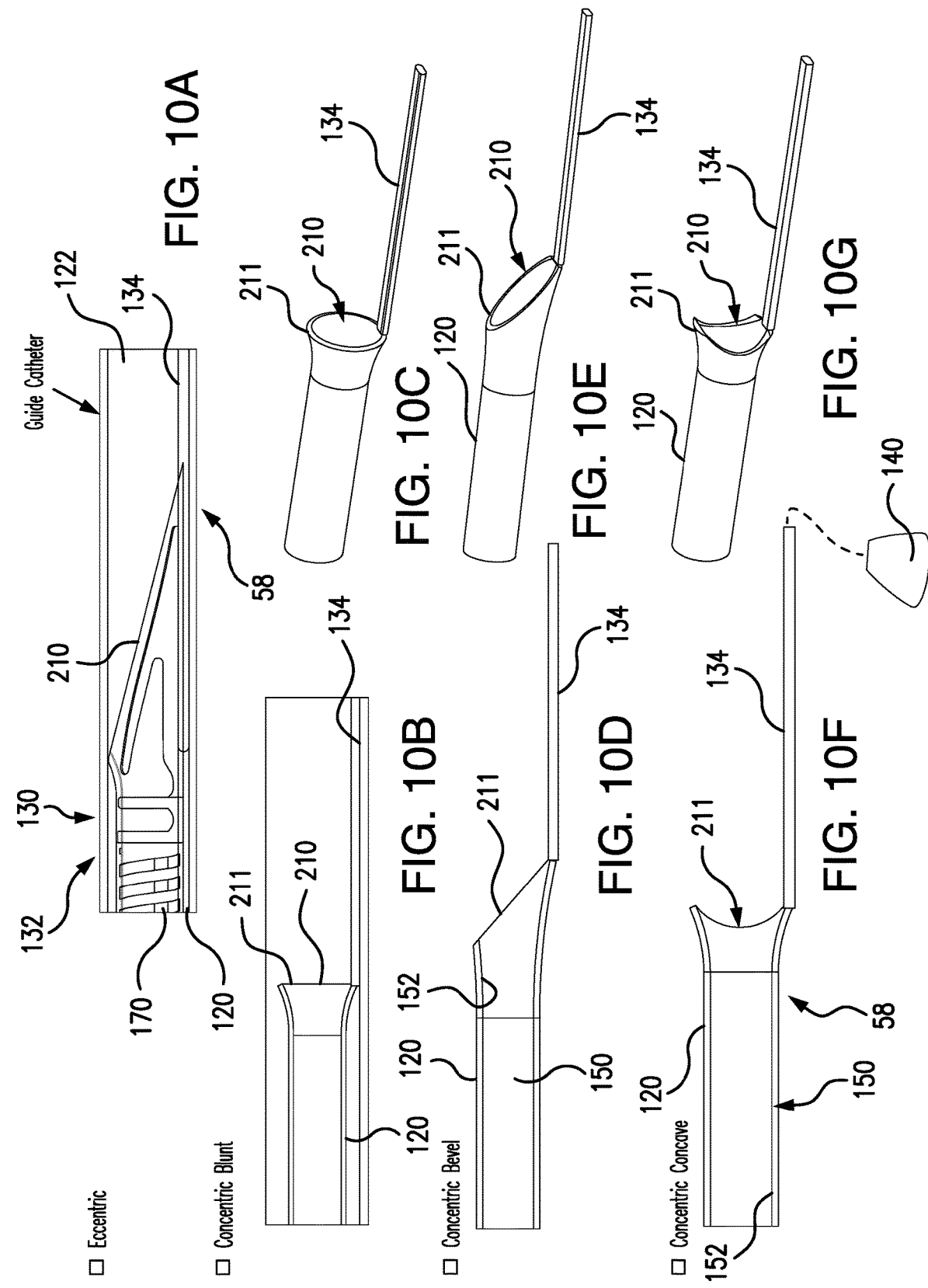

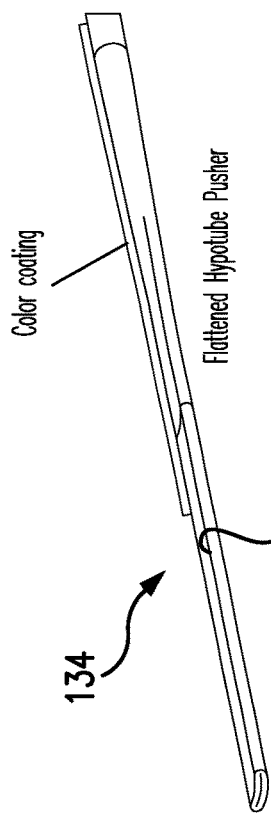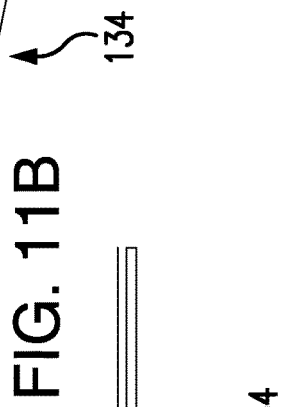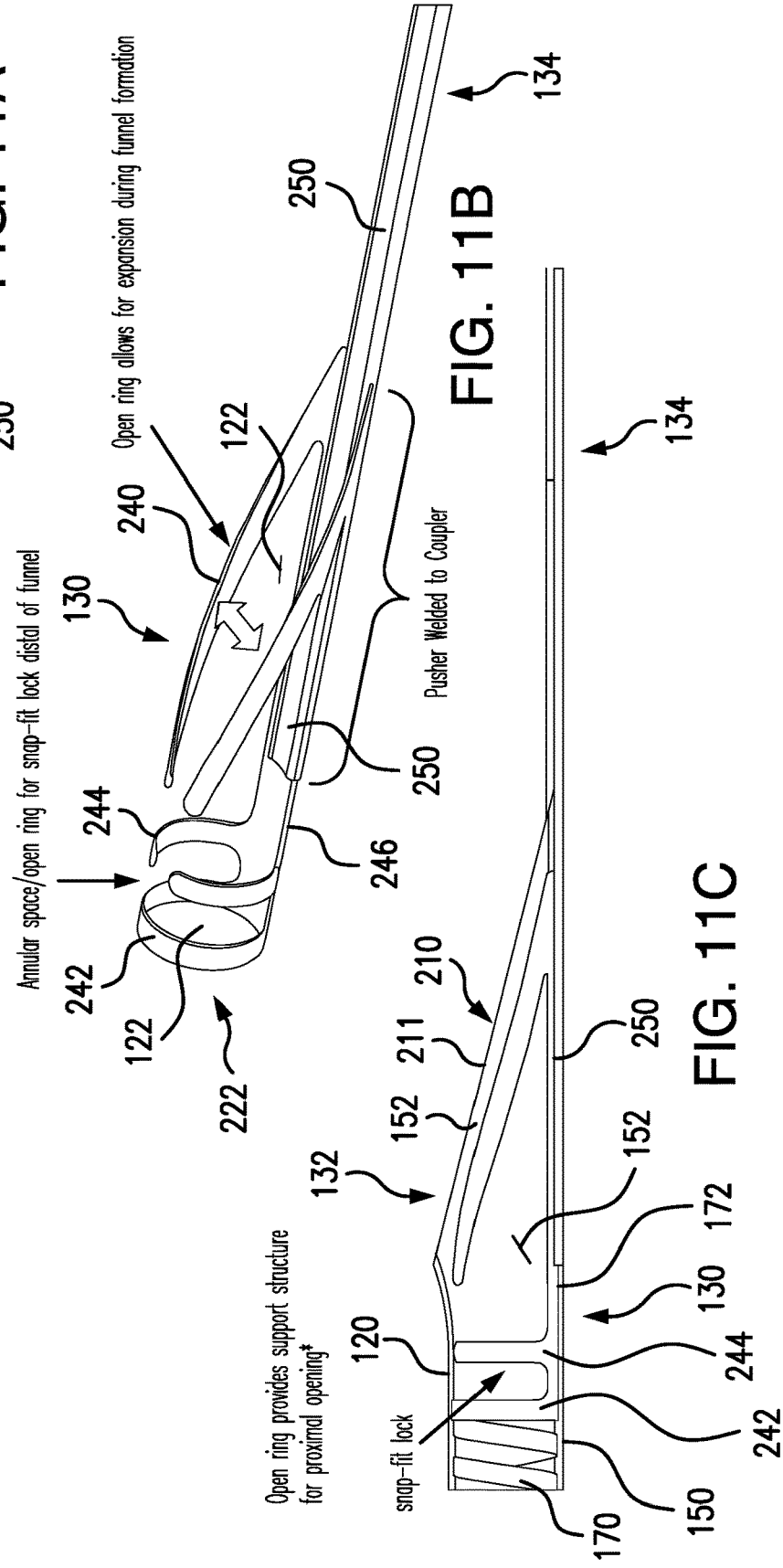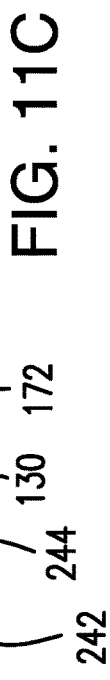

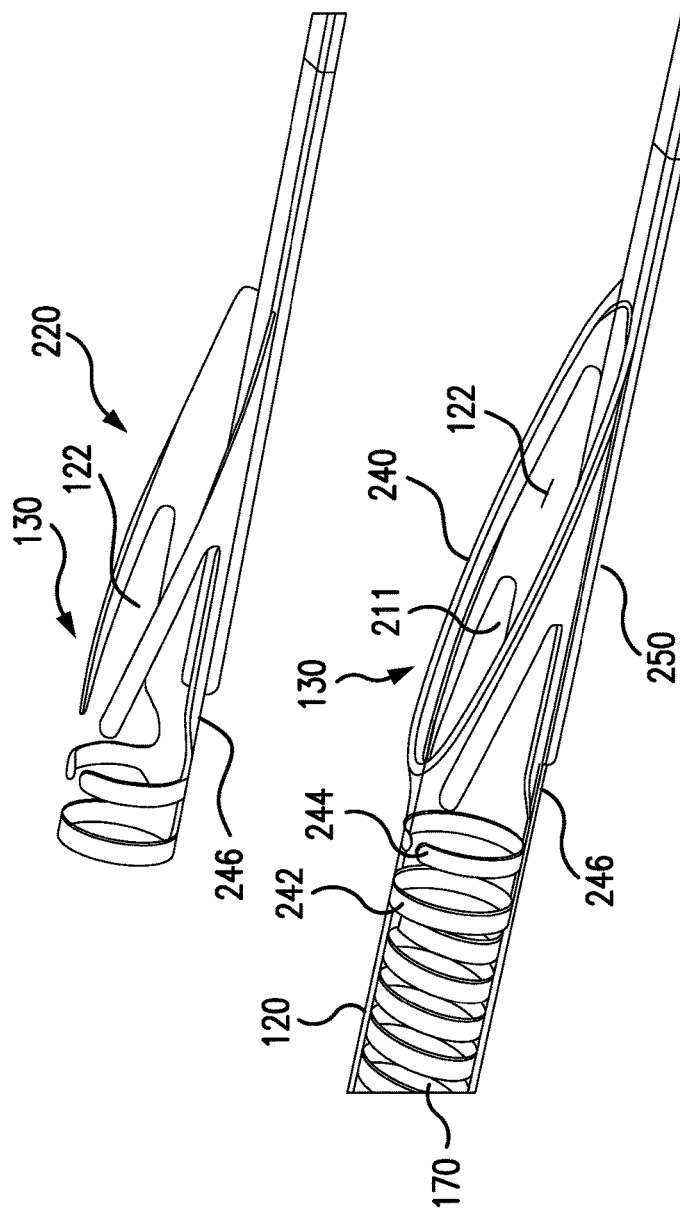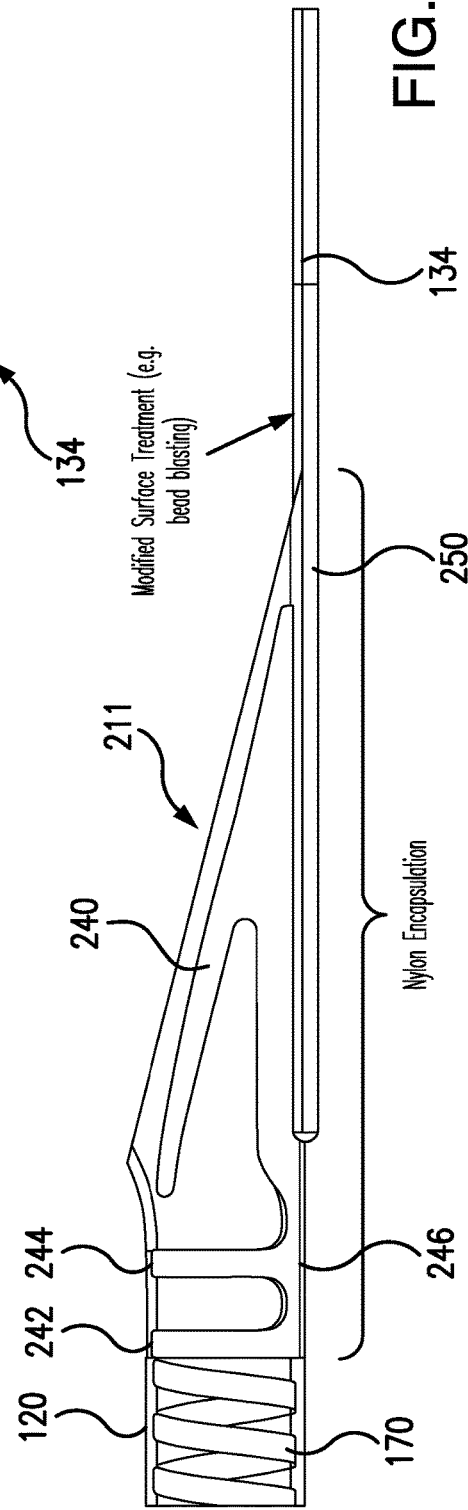

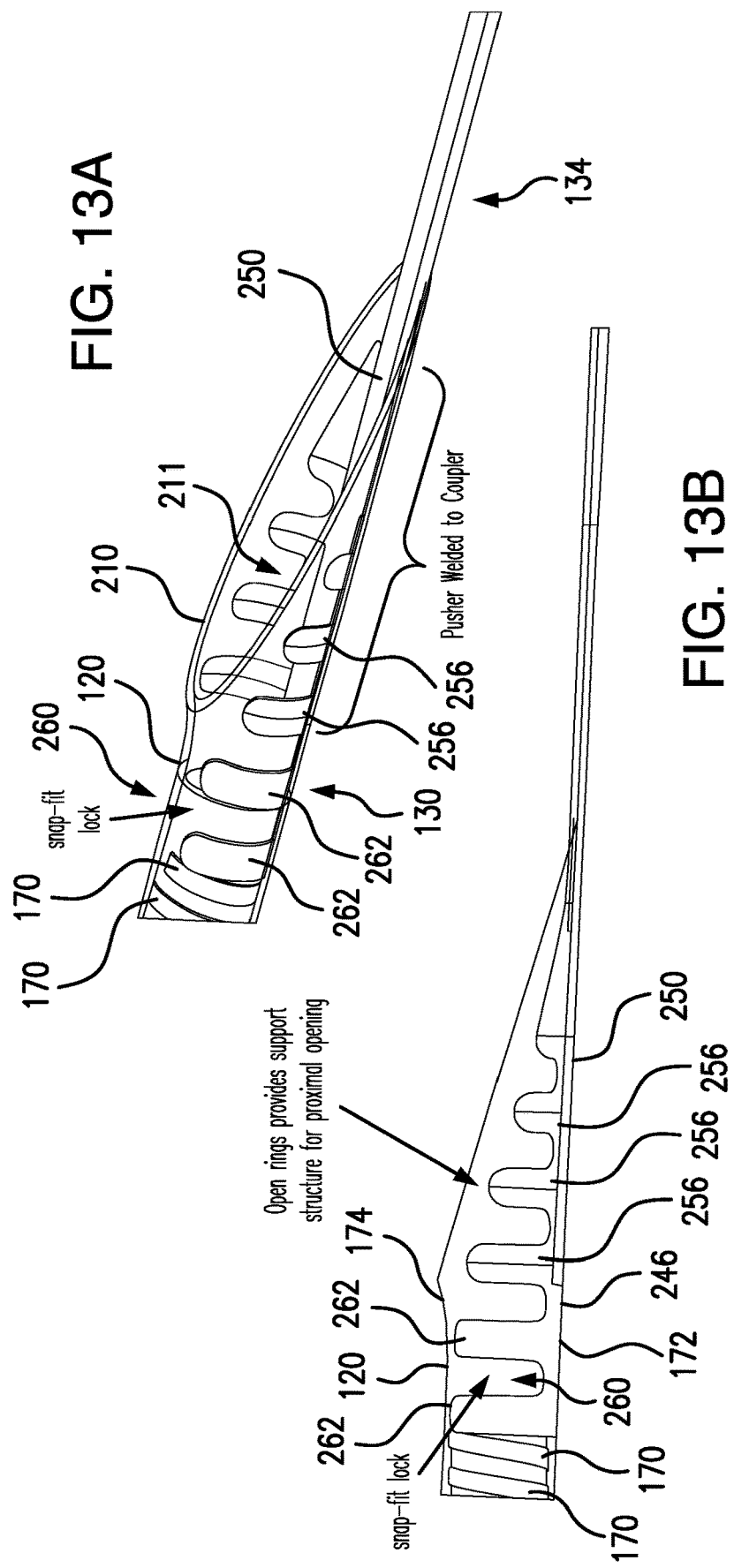

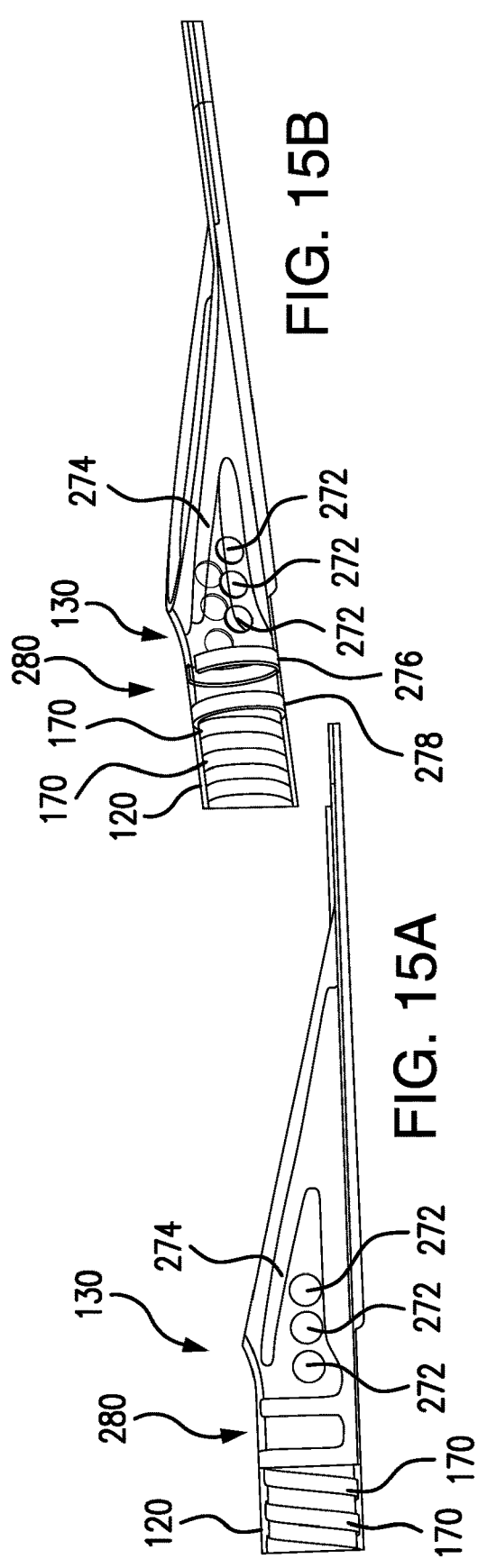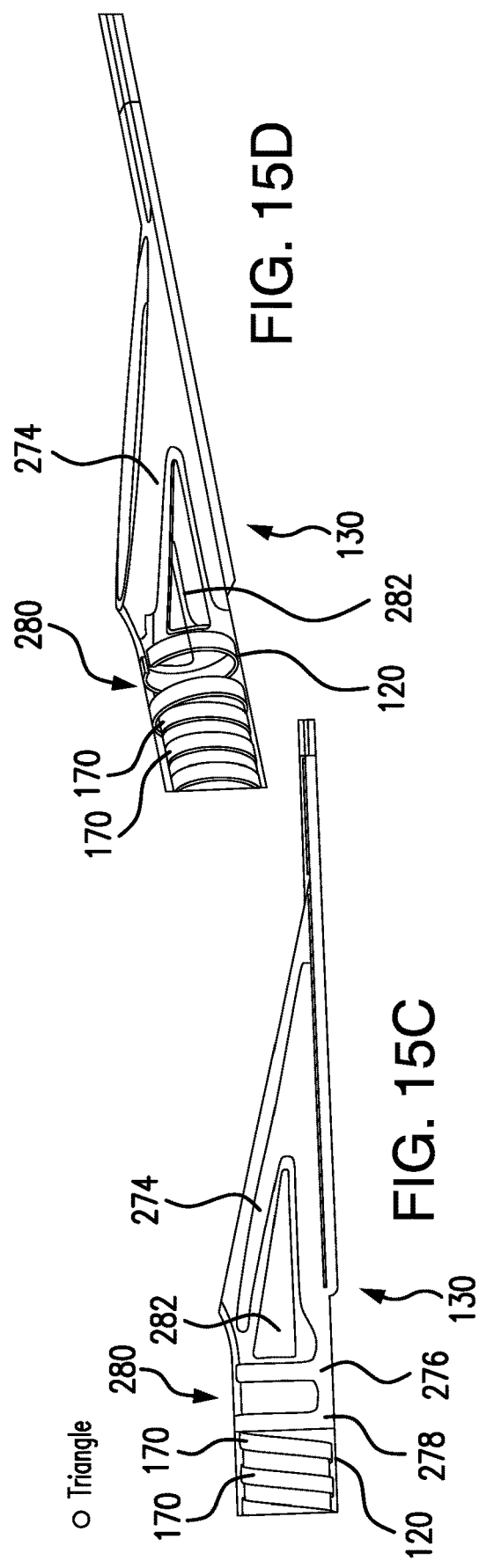

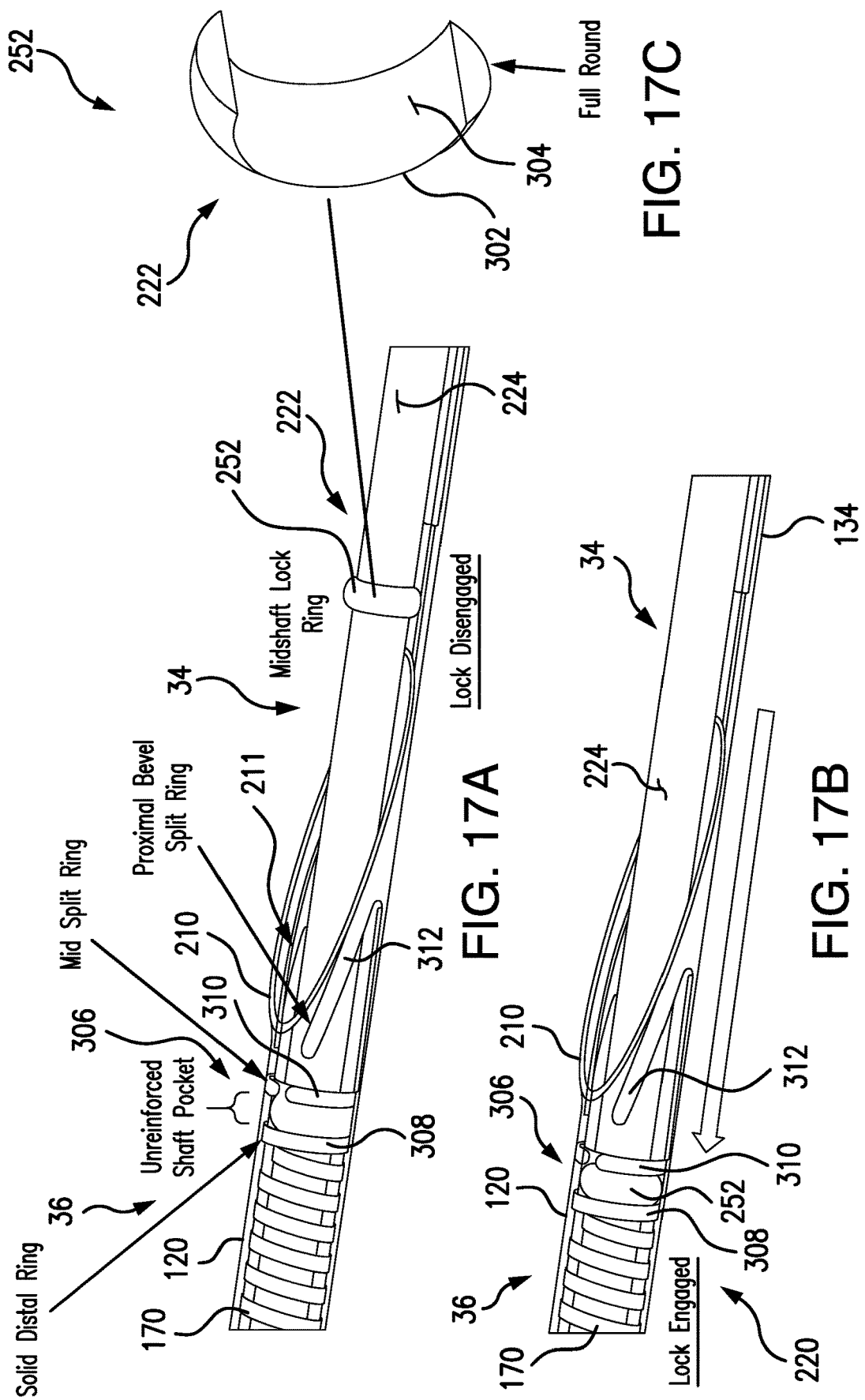

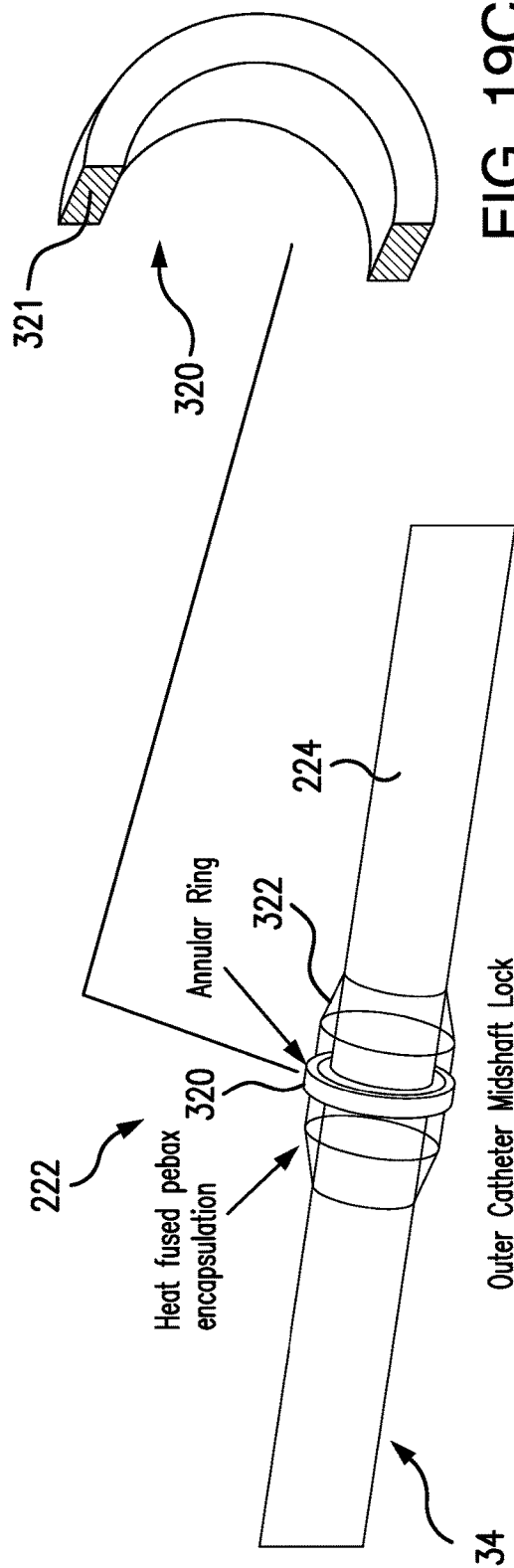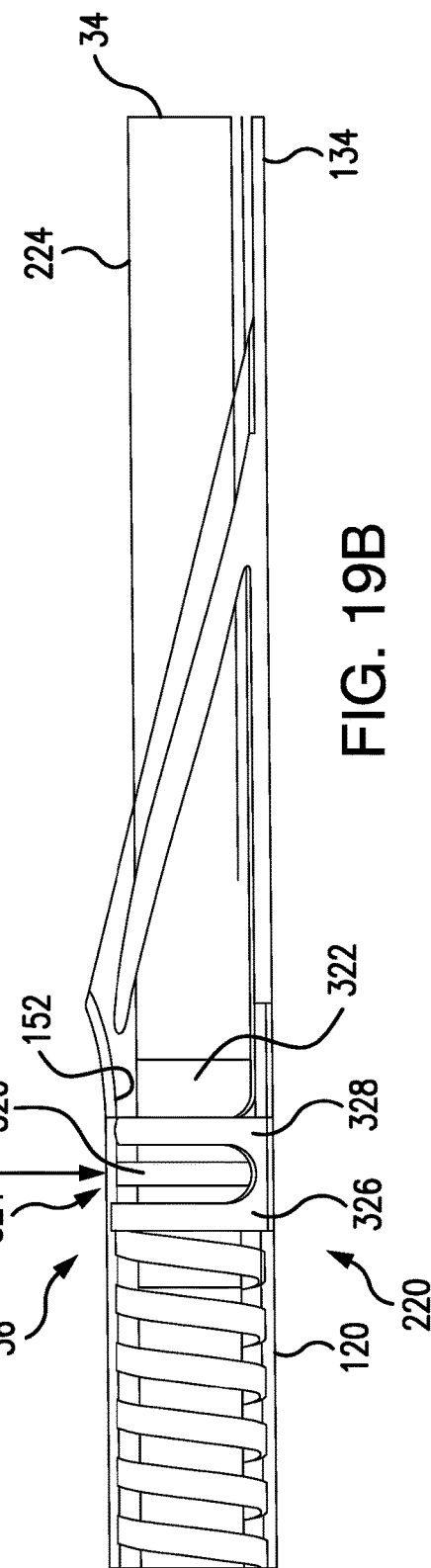

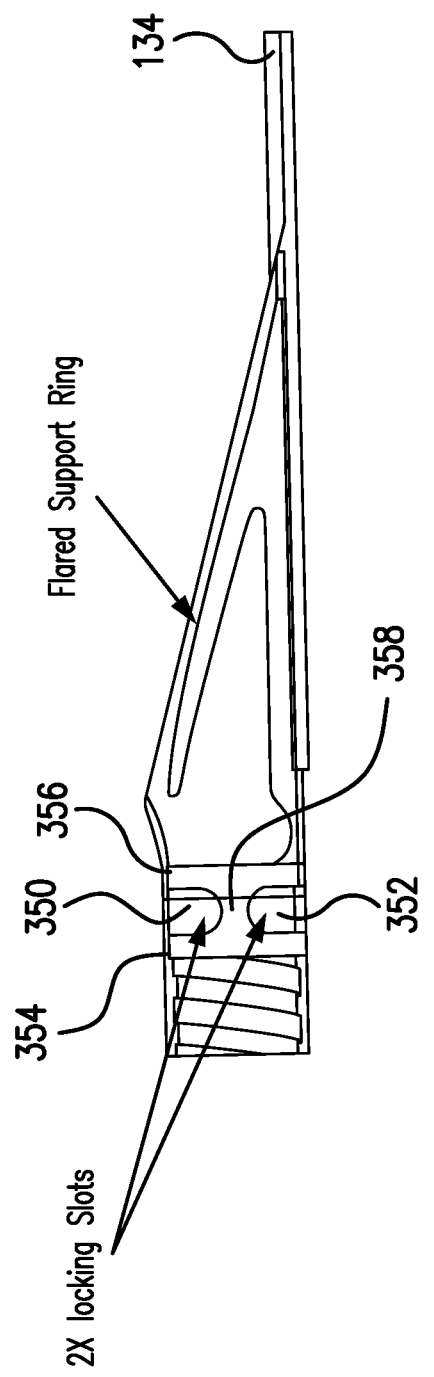

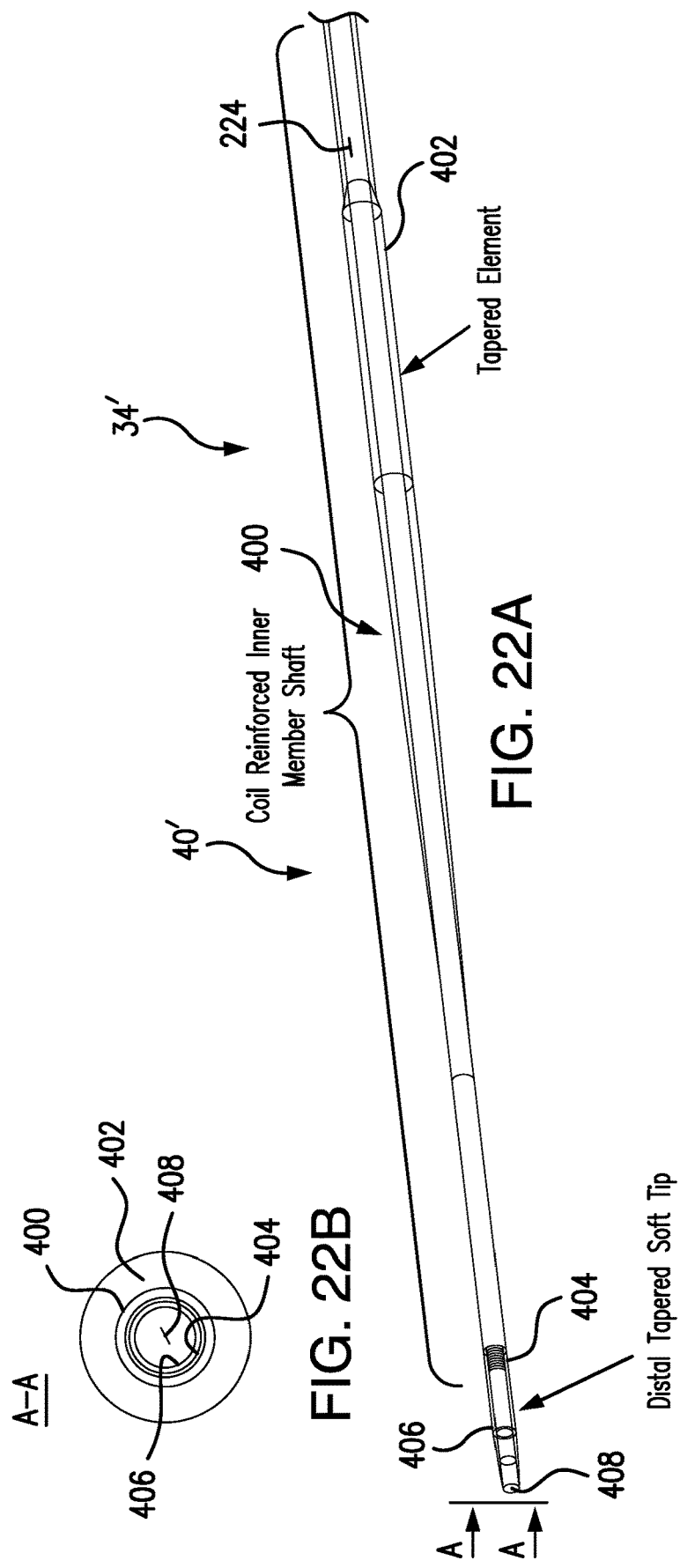

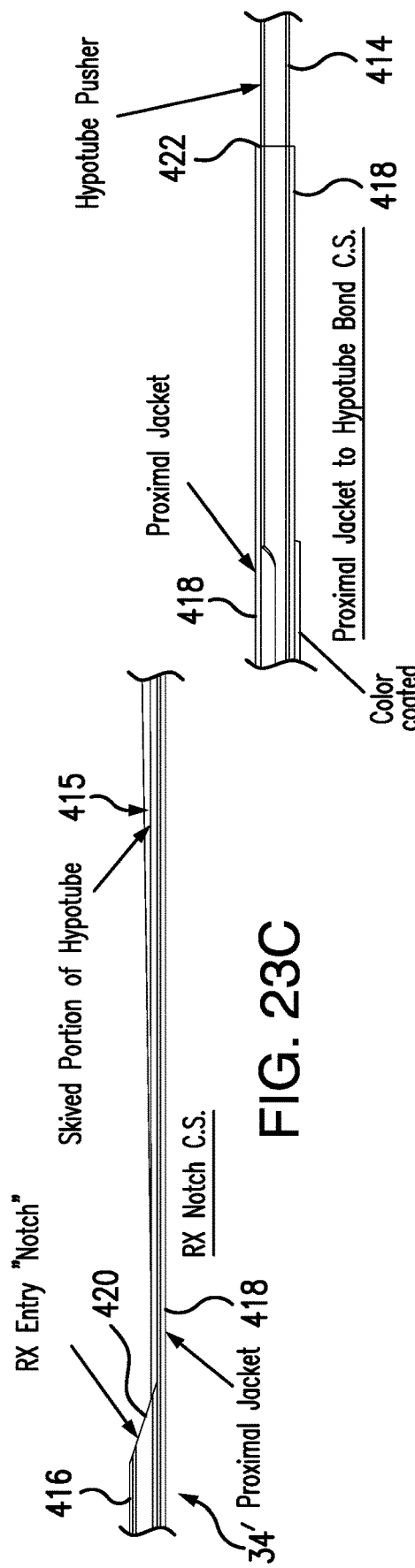

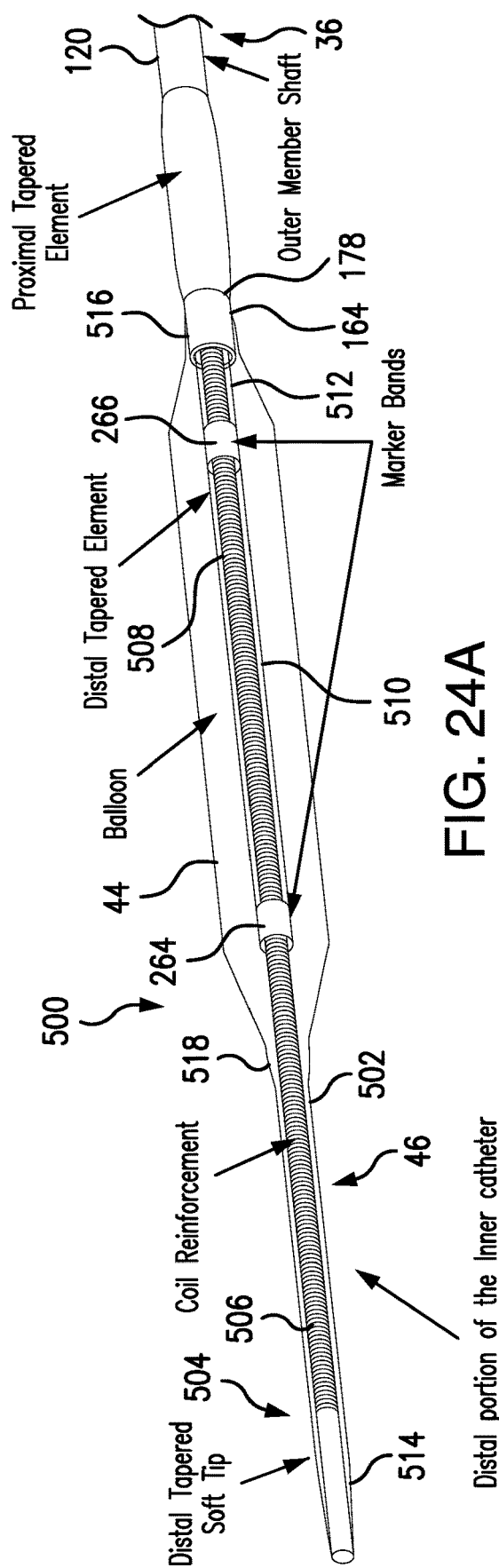
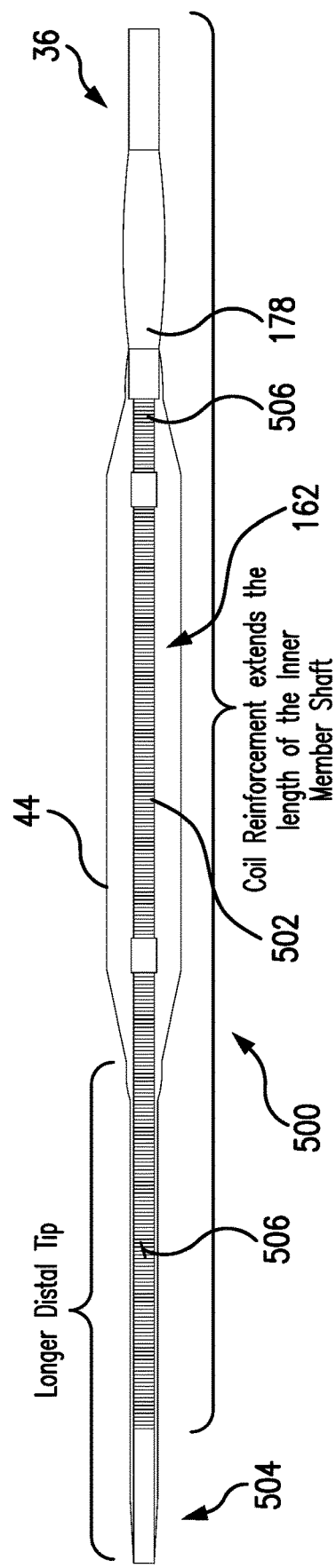
FIG. 24A
FIG. 24B

INTRAVASCULAR DELIVERY SYSTEM AND METHOD FOR PERCUTANEOUS CORONARY INTERVENTION

REFERENCE TO RELATED APPLICATIONS

The present Utility Patent Application is a Continuation of the Utility patent application Ser. No. 16/793,120, filed on 18 Feb. 2020, currently pending, which is a Continuation-in-Part (CIP) of U.S. Utility patent application Ser. No. 16/132,878, filed on 17 Sep. 2018, currently pending, which is a Continuation-in-Part (CIP) of U.S. Utility patent application Ser. No. 15/899,603, filed on 20 Feb. 2018, issued as U.S. Pat. No. 11,491,313.

INCORPORATION BY REFERENCE

U.S. patent application Ser. No. 16/132,878, and U.S. patent application Ser. No. 15/899,603, both currently pending, are hereby incorporated by reference.

FIELD OF THE INVENTION

The present invention is directed to minimally invasive devices used for treatment within the human vasculature, such as, for example, coronary arteries, and, in particular, to a delivery system for percutaneous coronary intervention adapted specifically for intravascular balloon angioplasty, and coronary artery stent delivery, enhanced by pre-dilatation guide catheter extension capabilities.

The present invention is also directed to medical devices designed for atraumatic, convenient and fast delivery of various interventional devices, such as, for example, a pre-dilatation balloon, or stents, and replacement of catheters in coronary arteries (or other blood vessels) in a patient's body to facilitate percutaneous revascularization.

The subject invention further addresses an intravascular delivery system which has a miniature tapered soft distal tip which is capable of an exceptional deliverability of the subject interventional device which is superior to that of the conventional balloon angioplasty catheters along with a practicably atraumatic crossability thereof to a site of a lesion for treatment.

The present invention is also directed to an intravascular guide catheter extension/pre-dilatation system using an inner member (interventional device delivery catheter sub-system) positioned at a predetermined location internal an outer member (the outer delivery catheter sub-system), where the inner member is formed with a distal coil reinforced tapered portion interfacing with a slightly tapered distal end of the outer member. These are dimensioned to form a miniature profile and a substantially "seamless" transition at the interface between the distal ends of the outer member (outer catheter) and the inner member (inner catheter), at the transition point where the inner catheter's distal portion engages or enters the outer member. This structure is greatly beneficial for an atraumatic and smooth passage of the inner and outer member as a single unit along a diseased blood vessel.

Additionally, the present invention is directed to an intravascular guide catheter extension/pre-dilatation system configured with an outer catheter (member) and an inner catheter (member) displaceable inside and along the outer catheter where a distal tapered soft tip of the outer catheter is formed as an expandable flexible low durometer elastomeric member which, in its reduced configuration, has an inner diameter less than the outer diameter of the distal portion of the inner catheter at the area of engagement with the outer catheter. This arrangement attains a reversible elastic engagement between the outer and inner catheters at their distal ends, which ensures a return of the expanded distal end of the outer catheter to its reduced outer diameter when the inner catheter has been removed from the outer catheter, and reduces (or eliminates) "fish mouthing" at the distal junction of the outer and inner members as the system is advanced around the bends of a blood vessel.

Further, the present invention is directed to an intravascular guide catheter extension/pre-dilatation system configured with an outer and inner catheters displaceable one relative to another, where the proximal end of the outer catheter has an entry configuration providing an enhanced reinforcement, enhanced mid-shaft stent entry, prevention of stent embolization, increased flexibility, and flow rate improvement for a contrast infusion fluid.

Furthermore, the present invention is directed to an intravascular guide catheter extension/pre-dilatation system designed with a mid-shaft interconnection (locking) mechanism which is actuated/de-actuated by a physician to either (1) controllably engage the inner and outer members for the integral motion within a guide catheter along a guide wire, or (2) disengage the inner and outer catheters for retraction of the inner catheter from the outer member (catheter), as required by the intravascular procedure. The inner member may carry an interventional device (such as a pre-dilatation balloon member, or a stent) attached at its tapered coil reinforced distal end, and the locking mechanism provides a smooth, reversible engagement/disengagement procedure. This mid-shaft reversible locking also prevents any forward movement of the inner member relative to the outer member during system advancement or withdrawal, and ensures that the position of the distal "seamless" transition of the inner and outer catheters remains essentially fixed in place axially during the movement of the subject system.

Additionally, the present invention is directed to an intravascular guide catheter extension/pre-dilatation system which is configured with a tapered coil reinforced shaft at its distal end for mounting and carrying a balloon member thereon and which provides a "seamless" entry and smooth deliverability of the balloon member integral with the outer catheter's coil reinforced delivery sheath to a desired treatment site.

The present invention further addresses an intravascular guide catheter extension/pre-dilatation system featuring a monorail micro-catheter embodiment with a Rapid Exchange (RX) feature for applications with short guidewires where the inner catheter's distal tapered soft end is configured with a coil-reinforced micro-catheter which provides additional kink resistance and "pushability" while still maintaining flexibility for navigating a tortuous vasculature.

BACKGROUND OF THE INVENTION

Coronary artery obstruction disease, or other disease in the peripheral vasculature, is often treated by a balloon angioplasty and/or stent placement. The advancement of revascularization devices, such as balloons or stent delivery systems, within blood vessels to a treatment site can be challenging to a physician where tortuosity and/or calcification of the vessels is found.

A coronary stent is a tube-shaped device placed in the coronary arteries that supply blood to the heart, to keep the arteries open for treatment of coronary heart disease which is used in a procedure commonly referred to as Percutaneous Coronary Intervention (PCI). Stents help to improve coronary artery blood flow, reduce chest pain and have been shown to improve survivability in the event of an acute myocardial infarction.

Treating a blocked coronary artery with a stent follows substantially the same steps as other angioplasty procedures, however there are important differences. The compressed stent mounted on a balloon significantly reduces the flexibility of the balloon and compromises its smooth advancement through the coronary artery. This can make it difficult or impossible to deliver the stent to a treatment site, and risks dislodgement of the un-deployed stent from its delivery balloon.

Intravascular imaging may be used to assess the lesion's thickness and hardness (calcification) which will affect the deliverability of the stent. A cardiologist uses this information to decide whether to treat the lesion with a stent, and if so, what kind and size of stent to be used. Stents, both bare metal and drug-eluting, are most often sold as a unit, with the stent in its collapsed (pre-expanded) form attached to the outside of a balloon catheter.

Physicians may perform "direct stenting", where the stent is threaded through the vessel to the lesion and expanded. However, it is common to pre-dilate the blockage before delivering the stent in order to facilitate the stent delivery in more challenging lesions.

Pre-dilatation is accomplished by threading the lesion with an ordinary balloon catheter and expanding it to increase the lesion's diameter. A balloon catheter is a type of "soft" catheter with an inflatable balloon at its tip which is used during a catheterization procedure to enlarge a narrow opening or passage within the body. Subsequent to pre-dilatation, the pre-dilatation balloon is removed, and a stent catheter is threaded through the vessel to the lesion and is expanded which is left as a permanent implant to "scaffold" open the vessel at the lesion site.

Balloon catheters used in angioplasty have either over-the-wire (OTW) or rapid exchange (RX) design. The balloon catheter slides to the location over the guidewire which can be charged into the balloon catheter through a hub (in the over-the-wire modification) or through an RX port (for the rapid exchange modification of the balloon catheter). In the over-the-wire balloon catheter, a concentric lumen for passing the guidewire extends within the catheter from the proximal hub to the balloon, while in the rapid exchange (RX) balloon catheter, the lumen for the guidewire passage extends from the RX port inside the catheter to the balloon to permit the passage of the guidewire.

Revascularization devices usually use guiding (or guide) catheters for delivery of such devices to the site of treatment. The use of guide catheters alone to "back up" the advancement of the revascularization devices to the coronary arteries may be limited and challenging, especially when stents are placed using a radial access guiding catheter.

In order to facilitate the revascularization devices delivery to the site of interest, guide catheter extension systems have been designed and used during cardiac procedures.

For example, the guide extension system, such as "Guideliner™," is produced by Teleflex. This guide extension system is described in U.S. Pat. No. 8,292,850, authored by Root, et al. Root, et al. (U.S. Pat. No. 8,292,850) and describes a coaxial guide catheter to be passed through a lumen of a guide catheter, for use with interventional cardiology devices that are insertable into a branch artery that branches off from a main artery.

The Root coaxial guide catheter is extended through the lumen of the guide catheter and beyond its distal end and inserted into the branch artery. Root uses the guide extension supported by a tapered inner catheter. The purpose of the inner catheter is to provide an atraumatic tip to avoid vessel injury, while advancing the guide extension into the proximal portion of a coronary vessel, in order to provide additional "backup" support for delivery of the stent or a balloon.

Another guide extension system, such as "Guidezilla™", has been designed and manufactured by Boston Scientific. This guide extension system is described in U.S. Pat. No. 9,764,118, authored by Anderson, et al. Anderson's guide extension system uses a push member having a proximal portion having a proximal stiffness, a distal portion having a distal stiffness different from the proximal stiffness, and a transition portion which provides a smooth transition between the proximal and distal portions. A distal tubular member is attached to the push member and has an outer diameter larger than the outer diameter of the push member.

U.S. Patent Application Publication #2017/0028178, authored by Ho, describes a guide extension system using a slit catheter which is extendable upon insertion of a balloon or stent delivery system. Ho's guide extension also uses a rigid push rod to assist in delivery of the guide extension to the treatment site.

The systems, "Guideliner™" and "Guidezilla™", as well as the Ho's system, support the concept of advancing the guide extension system through the guiding catheter, and partially down the coronary artery in order to achieve additional "back up" support to deliver balloon dilatation catheters and/or stent delivery catheters to the site of intended treatment.

The function of these guide extensions is to permit a closer approach to the lesion to provide additional support in crossing the lesion to be treated with an interventional device. However, despite the additional support, the lesion to be treated can still be difficult or nearly impossible to pass through with a pre-dilatation balloon catheter or a stent delivery system, due to fibrosis, calcification, prior stent struts in the lumen, and/or angulation at the lesion site.

One of the limitations of the currently used guide extension devices is that they use a relatively blunt and large caliber cylindrical distal end. Relatively high profile distal edges limit the deliverability of the guide extension in many cases, and permit the advancement only to the proximal or mid portion of the coronary artery to be treated. Very rarely, if ever, can the guide extension be delivered to the actual lesion to be treated with angioplasty or stenting, even after balloon pre-dilatation of the lesion. These "blunt-ended" tubular guide extension devices may fail relatively frequently, and may cause serious dissection complications. Published data demonstrate that "blunt-ended" tubular guide extension systems may fail it up to 20% of cases, and cause serious coronary artery dissections in ~3% of cases.

U.S. Patent Application Publication #2011/0301502, authored by Gill, describes a catheter with a longitudinal extension, allowing for the positioning device to be less in diameter than the stent delivery system. The Gill device, however, does not envision an inner catheter to permit easy and atraumatic crossing of the lesion to be treated. The Gill system acts merely as a covering for the stent delivery system, which can be removed after advancement of the stent delivery system due to the longitudinal extension.

Although the concept of a tapered piece inside a guide extension catheter is seen in the Root device, the prior art system uses a very short taper, and does not envision the taper as an elongated integrated member of the entire system, nor does it envision that a pre-dilatation balloon can be attached to the tapered delivery micro-catheter to be delivered to the target treatment area. In addition, the prior art fails to envision a substantially "flush" interface between the inner catheter and the outer guide extension inside the vessel, or that the inner and outer catheter members would be reversibly fit or locked together to allow the entire system to be moved easily as one integral device.

Root or other prior art systems do not describe, anticipate or envision a balloon (and/or stent) delivery system, with a very low profile elongated tip which would be beneficial in attaining the coaxial delivery of the guide catheter extension/balloon system to, and beyond, a lesion of interest. Such an embodiment has never been commercialized, and the description of the tapered tip inner device was only meant as a mechanism for the proximal delivery of the blunt tip of the guide catheter extension out of the guiding catheter, but never as a mechanism for delivery of a balloon (and/or stent) to, and beyond, the target treatment area in a blood vessel, nor does it envision that the integral nature, and "flush" interconnection, of the inner and outer members would allow the passage of the outer delivery "sheath" member to cross the lesion of interest.

Thus, a device and method that would permit a delivery of the distal portion of the tubular guide extension system to, or ideally, beyond, the lesion to be treated, would have significant advantages over conventional guide extension devices, such as the "Guideliner™" (Teleflex), or the "Guidezilla™" (Boston Scientific), and others.

Neither of the conventional balloon catheters (over-the-wire or rapid exchange) is integrated with an outer delivery sheath, and neither of them uses a tapered delivery micro-catheter at the distal end of the catheter to which an interventional device (such as the balloon, or stent, etc.) would be secured for atraumatic advancement inside the blood vessel to, and beyond, the lesion site. In addition, none of the conventional balloon catheters is interconnected with an outer delivery sheath (guide catheter extension sub-system) via an interconnection mechanism actuated to permit integral motion of the conventional balloon catheter and the outer delivery sheath as a single unit, and deactuated to permit retraction of the balloon catheter from the outer delivery sheath, while preventing a forward displacement of the balloon catheter relative the outer delivery sheath.

It would be highly desirable, and efficient, to provide an intravascular delivery system which is capable of delivering an interventional device (for example, a pre-dilatation balloon) along with a guide catheter extension sub-system (such as an outer delivery sheath) to, and beyond, the lesion in a substantially atraumatic and convenient manner.

It also would be highly desirable to provide an intravascular delivery system which has an outer catheter and an inner catheter both featuring reinforced distal ends having a miniature tapered distal tip profile with a "seamless" distal interface to ensure an atraumatic crossability of the system to a lesion for treatment.

In addition, it would be desirable to facilitate percutaneous revascularization procedures by using a balloon attached to a coil reinforced tapered distal tip of the inner balloon catheter which is fitted within the outer delivery sheath of the outer catheter, where the inner balloon catheter is equipped with a distal elongated tapered coil-reinforced micro-catheter at the tapered distal tip to carry an interventional device (the pre-dilatation balloon, and/or stent) to, and past, the lesion to be treated. This would represent substantial improvement upon conventional guide catheter extension and pre-dilatation systems.

SUMMARY OF THE INVENTION

It is therefore an object of the present invention to provide a medical device for intravascular applications that is capable of delivery of an interventional device (such as a balloon or a stent) to, and beyond, a coronary artery obstructive lesion in an efficient and minimally traumatic fashion.

It is another object of the present invention to provide an intravascular delivery system using a coaxial, highly flexible delivery catheter arrangement with an outer catheter and an inner catheter interfacing with each other at their distal ends in a "seamless" fashion with a miniature profile which is beneficial in attaining a "crossability" of the pre-dilatation balloon (or other interventional device), and enhances the efficient and safe distal delivery of a guide extension device.

It is an additional object of the subject invention to use a highly flexible coil-reinforced distal tapered elongated micro-catheter tip to deliver a pre-dilatation balloon (or another interventional device) to, and/or beyond, a target lesion in a diseased human coronary artery to be treated with angioplasty (or stenting).

It is a further object of the present invention to provide a guide catheter extension/pre-dilatation system using an outer catheter (outer delivery sheath sub-system) and an inner catheter (interventional device delivery sub-system) fitted and interchangeably connected within the outer sheath of the outer catheter, both deliverable to, or beyond, the lesion area of treatment within a blood vessel where the inner catheter has a delivery tapered micro-catheter at its distal end with the pre-dilatation balloon member (or another interventional device) attached thereto which slides along a guidewire in a substantially atraumatic manner.

It is a further object of the present invention to provide a guide catheter extension sub-system (outer member) integrated with the pre-dilatation balloon (or another interventional device) sub-system (inner member), in which the outer member and the inner member are coupled each to the other (via a locking mechanism) to be integrally (as a "whole system") displaced along the guidewire to a lesion site. After the pre-dilatation procedure, the guide catheter extension sub-system (configured with an outer delivery sheath) is unlocked from the inner member and may be, if desired, advanced beyond the lesion. Subsequently, the inner member (interventional device delivery sub-system) may be withdrawn. The outer delivery sheath of the outer member may, if needed for the surgical procedure, remain in the guide catheter to enhance the deliverability of a stent (or other interventional device) to the lesion site inside the outer delivery sheath. The outer delivery sheath may be subsequently withdrawn after the stent (or other interventional device) has been delivered to the lesion and deployed for a definitive treatment.

Furthermore, it is an object of the present invention to provide a guide catheter extension/pre-dilatation system equipped with a "locking mechanism" operatively coupled between the inner member and the outer member (outer sheath) to provide integral passage of both the inner and outer members, as a single unit, for convenient and safe deliverability of the pre-dilatation balloon and the outer sheath to, and beyond, a treatment site.

It is a further object of the present invention to provide a guide extension system configured with the pre-dilatation balloon (or other interventional device) delivery catheter deliverable to the treatment site inside a vascular structure in an atraumatic manner to attain easy passage of the balloon (or other interventional device) and the guide extension system therethrough, thus expediting the cardiac procedure which permits percutaneous coronary intervention to be performed with a lower radiation dose exposure than would be achieved using conventional systems, with the added advantage of virtually no risk of stent embolization, or drug loss (with drug-eluting stents) from the stent delivery system.

A further object of the subject invention is to provide an intravascular guide catheter extension/pre-dilatation system configured with coaxial inner and outer catheters displaceable relative one another and enhanced by a coil reinforcement along their length, yet being increasingly flexible, and capable of attaining an improved contrast infusion flow rate and embolization prevention, where the tapered distal end of the outer catheter can be elastically stretched to form a strong contact with the distal portion of the inner catheter and nearly flush (smooth) outer surface at the interface between the inner catheter and the outer catheter.

The present system and method addresses an intravascular delivery system configured for controllable displacement along a guide wire in a blood vessel of interest. The subject system is formed with a proximal section, a distal section, and a middle section portion located between the proximal and middle sections. The current system includes an outer member formed by a flexible substantially cylindrically contoured elongated outer delivery sheath defining a sheath lumen having a proximal end and a distal end. The outer delivery sheath extends between the middle section and distal section and is configured with a tapered outer tip at the distal end of the sheath lumen. The tapered outer tip of the outer member at the distal end of the outer delivery sheath is configured with a wall extending in a cylindrical manner between a distal edge and a proximal edge of the tapered outer tip. The wall of the tapered outer tip has an inner diameter and an outer diameter. The inner and outer diameters of the wall of the tapered outer tip are gradually reduced in dimension from the proximal edge to the distal edge of the tapered outer tip. The proximal (wire or hypotube) element (pushing or pulling) connected to the outer member's tubular structure may be low profile and "flexible" (not "rigid") to allow an enhanced conformability inside the guiding catheter and a lower profile than the rigid "pushing" elements in conventional guide extension catheters (as per Root). This is made possible due to the "pushability" of the "system as a whole", attained via the locked and integral connection between the outer catheter (with its hypo-tube pushing/pulling element) and the inner catheter (guide extension tube).

The subject system further includes an inner member (inner catheter) having an elongated body defining an internal channel extending along its longitudinal axis. The inner member extends internally along the sheath lumen of the outer member (outer catheter) in a controllable relationship with the outer delivery sheath. The elongated body of the inner member has a tapered distal portion having an outer diameter and configured with a tapered delivery catheter having an elongated body of a predetermined length. The tapered delivery catheter of the inner member is displaceable beyond the distal end of the outer sheath. It is important that the inner diameter of the wall of the tapered outer tip of the outer member is less than the outer diameter of the tapered distal portion of the inner member at the area where the two elements form a distal junction.

An interconnection mechanism is operatively coupled between the inner and outer members and is controllably actuated to operate the guide catheter extension/pre-dilatation sub-system in an engaged or disengaged mode of operation. In the engaged mode of operation, the inner and outer members of the guide catheter extension sub-system are engaged for a controllable common displacement along the guide wire. This also allows the enhanced "pushability" of the subject system (with the outer member connected and locked to the inner member) even with the connected pusher (pushing/pulling element) of the outer member having a miniature profile and being flexible (as flexible or more flexible than the outer tubular sheath of the outer catheter). In the disengaged mode of operation, the inner and outer members are disengaged for retraction of the inner member from the outer member subsequent to the pre-dilatation treatment, or stent, delivery.

The distal portion of the inner member interfaces, at the outer surface thereof, with an inner surface of the tapered outer tip of the sheath lumen. A dimensional transition between the outer diameter of the outer tip of the sheath lumen and the outer diameter of the distal tip of the inner member forms a substantially flush interface transition therebetween.

The tapered outer tip of the outer member has an elastically expandable configuration. At the proximal end thereof (also referred to herein a mid-shaft portion of the outer member), the outer sheath is configured with an entrance opening exceeding in its circumference the circumference of the tubular body of the outer sheath. In some embodiments, the entrance opening at the proximal end of the outer sheath is funnel shaped.

The outer sheath is preferably reinforced along its length. The outer member comprises a distal soft tip encapsulating material enveloping the reinforced sheath of the outer member at its distal end. The distal soft tip encapsulating material is a flexible low durometer elastomeric material having a gradient durometer value increasing from the distal end towards the proximal end of the sheath.

The outer member also includes a distal lubricous liner sandwiched between an outer surface of the outer sheath and an inner surface of the distal soft tip encapsulating material.

The delivery catheter is preferably a micro catheter. The micro-catheter is formed of a flexible material and may have a differential flexibility along its length, wherein the flexibility of the micro-catheter increases towards its distal end.

A balloon member is attached to the tapered distal portion of the inner member in proximity to the tapered delivery micro-catheter; and an inflation lumen extends within the inner member between the proximal section and the balloon member at the distal section to provide a fluid passage between an external balloon inflation system and the balloon member. The balloon member may assume an inflated configuration or a deflated configuration. In the deflated configuration, the balloon member is displaced in the blood vessel. The balloon member is controllably transformed into the inflated configuration subsequent to being positioned at least in alignment with the treatment site for the pre-dilatation procedure.

The elongated body of the inner member and the micro-catheter are coil reinforced along their length.

An outer catheter's pusher/puller element configured with a flattened portion at its distal end is secured to the proximal end of the outer sheath of the outer catheter. Preferably, the outer member's pusher/puller is configured with a channel extending along its length in fluid communication with the sheath lumen in order to prevent embolization. This proximal (pushing and pulling) element connected to the outer catheter's outer sheath tubular structure may be low profile and "flexible" (not "rigid") to allow better conformability inside the guiding catheter and a lower profile than the rigid "pushing" elements in conventional guide extension catheters (such as Root).

The interconnection mechanism may include a snap-fit locking mechanism configured with a proximal coupler disposed at the proximal end of the sheath of the outer member (catheter) and a cooperating element disposed at the outer surface of the elongated body of the inner member (catheter). The proximal coupler may include a distal solid ring and a mid split ring positioned a predetermined distance from the solid ring, while the cooperating member includes a member selected from a group including a mid-shift lock ring, square annular ring, snap-fit cage and other like members. The cooperating member is affixed to the outer surface of the elongated body of the inner member. When the cooperating member is engaged and locked in a snap-fit fashion between the distal solid ring and the mid split ring, a locking engagement between the outer and inner members is attained. The proximal pusher/puller element of the outer catheter and the coupler may be made from a memory metal (such as, for example, nitinol), so as to prevent deformation during the antegrade or the retrograde movement of the outer member and to prevent any deformation of the mid-shaft coupler (also referred to herein as a proximal coupler) during the stent or other device passage through the mid-shaft portion of the outer catheter.

The proximal coupler further includes a proximal beveled split ring at its proximal end which reinforces the funnel like proximal entrance of the outer member and prevents damage or permanent deformation of the funnel shaped proximal entrance caused by displacement of the inner member or a stent delivery system in the funnel entrance. The coupler and mid-shaft entry may have an entrance opening (or a "mouth") the circumference of which is larger than the circumference of the outer member's flexible tubular outer sheath structure.

The subject intravascular system further includes a guide wire advanceable in a blood vessel of interest to at least a treatment site, wherein the guide catheter extension subsystem is configured for controllable displacement along the guide wire. In one of the subject system's embodiments, an elastic outer jacket envelopes the inner member, at least at its proximal end, and the inner member's pusher/puller along at least its distal end. The proximal end of the inner member is connected to the pusher/puller by fusing the elastic outer jacket to the length of the proximal end of the inner member and supporting the inner member's pusher/puller snuggly in the elastic outer jacket.

The pushing-pulling element (or its outer jacket) of the outer catheter may be color coated to have a distinguished color to differentiate it from the pushing/pulling element of the inner catheter, as well as from the usual gray or silver color of a coronary guidewire. Alternatively, the elastic outer jacket of the inner member may be color coated to distinguish the inner member's pusher/puller from the color(s) of other elements in the subject system for the surgeon's convenience.

These and other objects and advantages of this invention will become apparent to a person of ordinary skill in this art upon reading the detailed description of the subject invention in conjunction with the Patent Drawings.

BRIEF DESCRIPTION OF THE DRAWINGS

FIGS. 2A-2C schematically describe the subject guide catheter extension/pre-dilatation system, where FIG. 2A shows the assembled inner and outer catheters, FIG. 2B details the inner catheter, and FIG. 2C details the middle section of the subject system;

FIGS. 5A-5C depict the distal section of the subject system with FIG. 5A depicting the inflated balloon member, FIG. 5B presenting the deflated balloon member, and FIG. 5C detailing the inflation lumen/balloon junction;

FIGS. 6A-6B depict the longitudinal section of the distal section of the subject inner catheter detailing the balloon's 3 mm distal and proximal tapers (FIG. 6A) and the balloon's 6 mm distal and proximal tapers (FIG. 6B);

FIGS. 8A-8B detail the interfacing of the inner and outer catheters at their distal ends, where FIG. 8A is representative of the inner catheter's tapered distal end, and FIG. 8B depicts on a somewhat enlarged scale, the connection point between the inner and outer catheters;

FIGS. 10A-10G depict a side view (FIGS. 10A, 10B, 10D, 10F), and an isometric view (FIGS. 10C, 10E, 10G) of the alternative embodiments of the proximal portion of the subject outer catheter;

FIGS. 11A-11C detail the design of the coupler at the proximal end of the outer catheter, where FIG. 11A depicts an isometric view of the flattened hypo-tube pusher, FIG. 11B is an isometric view of the proximal end of the outer catheter, and FIG. 11C depicts a side view of the coupler at the proximal end of the outer catheter featuring a snap-fit lock mechanism;

FIGS. 12A-12C depict an alternative embodiment of the proximal portion of the subject outer catheter, with FIG. 12A being an isometric view of the proximal coupler, FIG. 12B being an isometric view of the encapsulated proximal coupler, and FIG. 12C being a side view of the encapsulated proximal coupler;

FIGS. 13A-13B illustrate an isometric view (FIG. 13A) at a side view (FIG. 13B) of yet another embodiment of the proximal coupler at the outer catheter's proximal end;

FIGS. 15A-15D depict additional alternative embodiments of the proximal coupler of the outer catheter, with FIG. 15A-15B being a side view and isometric view, respectively, of the circularly contoured funnel fenestrations, and FIGS. 15B-15D being a side view and isometric view, respectively, of the triangular funnel fenestrations;

FIGS. 17A-17C depict the subject mid-shaft annular round ring lock mechanism, where FIG. 17A shows the "lock disengaged" mode of operation, FIG. 17B illustrates the "lock engaged" mode of operation, and FIG. 17C is representative of the annular round ring in the subject lock mechanism;

FIG. 18A depicts the proximal coupler configured with the lock pocket for engagement with the annular round ring (of FIG. 17C), and FIG. 18B is a longitudinal cross-section of the inner/outer catheters locked one to another;

FIGS. 19A-19C depict the alternative subject embodiment of the lock mechanism, featuring a mid-shaft "square" annular ring, with FIG. 19A illustrating the inner catheter equipped with the ring shaped lock mechanism, FIG. 19B illustrating the inner catheter's ring snapped in the outer catheter's proximal coupler, and FIG. 19C depicting a cross-sectional view of the square annular ring;

FIG. 21 is a side view of another embodiment of the outer catheter's proximal coupler featuring two locking slots;

FIG. 22A-22B are representative of a monorail micro-catheter embodiment of the subject system with FIG. 22A depicting an isometric view of the monorail micro-catheter embodiment, and FIG. 22B showing a side view taken along Lines A-A;

FIG. 23A-23C detail the subject monorail micro-catheter embodiment with FIG. 23A showing the isometric view of the proximal portion of the inner catheter connected with the inner catheter hypo-tube pusher, FIG. 23B detailing the proximal end of the pusher on a somewhat enlarged scale, and FIG. 23C being a side view of the proximal portion of the inner catheter connected with the hypo-tube pusher; and FIGS. 24A and 24B depict an isometric view and a side view, respectively, of the coil reinforced balloon catheter embodiment of the subject system.

DETAILED DESCRIPTION OF THE PREFERRED EMBODIMENTS

Depicted in FIGS. 1-24B, is the subject intravascular delivery system 10 which includes a guide catheter extension sub-system (also referred to herein as an outer catheter or an outer member) and an interventional device delivery sub-system (also referred to herein as an inner catheter or an inner member) cooperating under control of a surgeon during a cardiac procedure. Although the interventional device delivery sub-system may be used for delivery of various cardiac interventional devices, in one of the implementations, as an example only, but not to limit the scope of the subject invention to this particular embodiment, the subject interventional device delivery sub-system will be further described as adapted for delivery of a balloon member for performing the pre-dilatation procedure.

Figure 1:
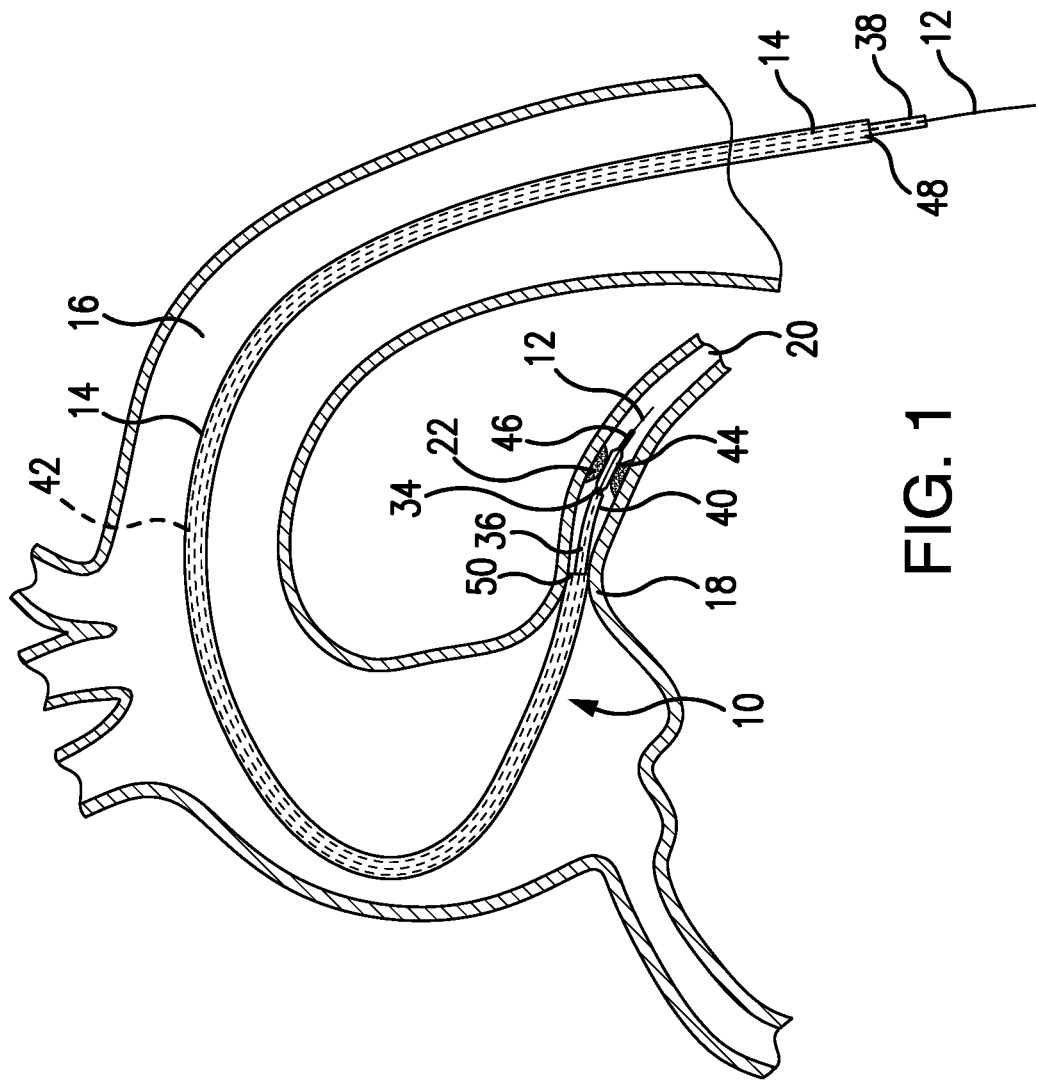
FIG. 1 schematically represents the subject guide catheter extension/pre-dilatation system advanced to the target site within a coronary artery.

In the exemplary embodiment described herein, the subject system 10 may be referred to herein as a guide catheter extension/pre-dilatation system which may be used for cardiac procedures in conjunction with a guide wire 12 and a guide catheter 14. As shown in FIG. 1, at the initial stage of the cardiac procedure, the guidewire (GW) 12 is moved by a surgeon into the blood vessel 16. The guide catheter 14 is advanced through the blood vessel 16 (such as, for example, the aorta) along the guide wire 12 to a position adjacent to the ostium 18 of the coronary artery 20. The guidewire 12 may be used during the cardiac procedure to guide the guide catheter 14, and, subsequently, the subject guide catheter extension/pre-dilatation system 10 (inside the guide catheter 14) may be extended within the artery 20 toward a target location 22, as will be detailed in following paragraphs.

Figure 2A:
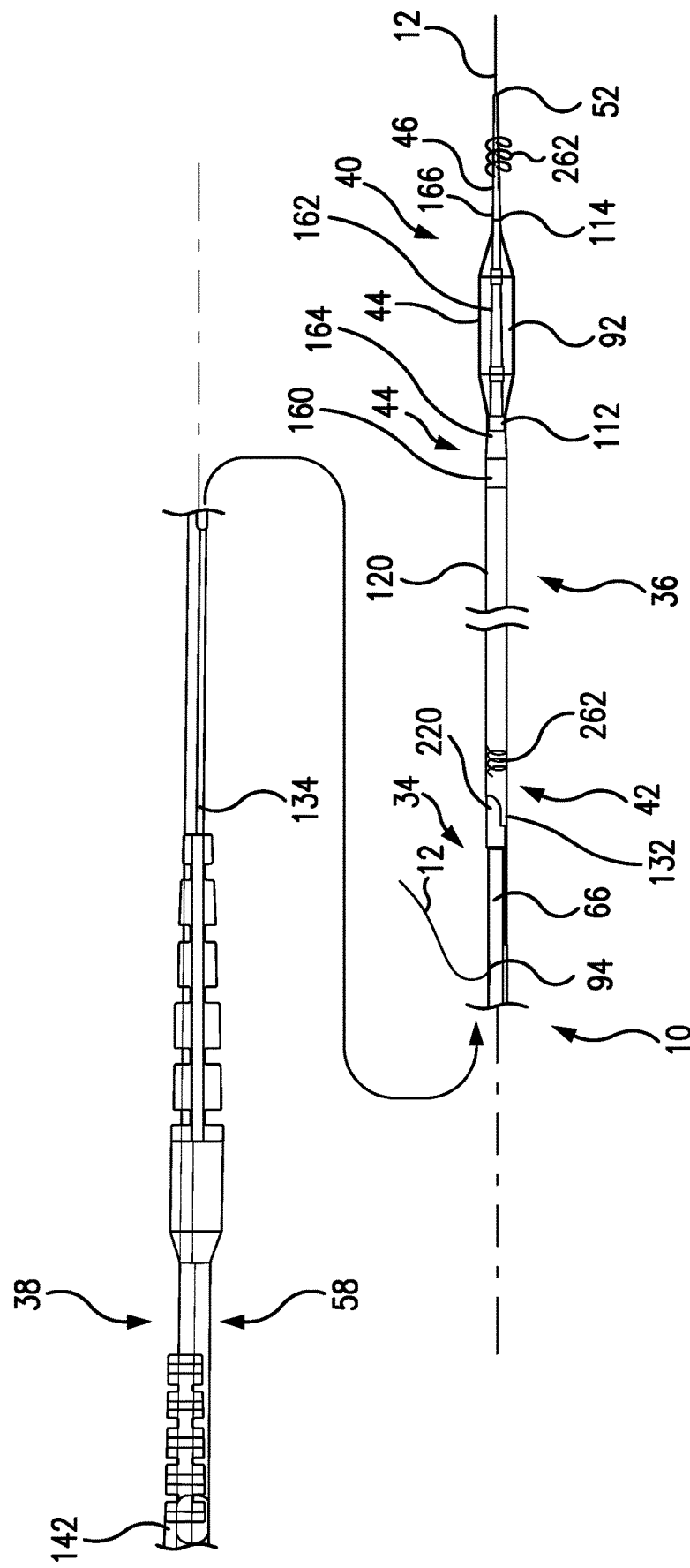
Figure 2C:
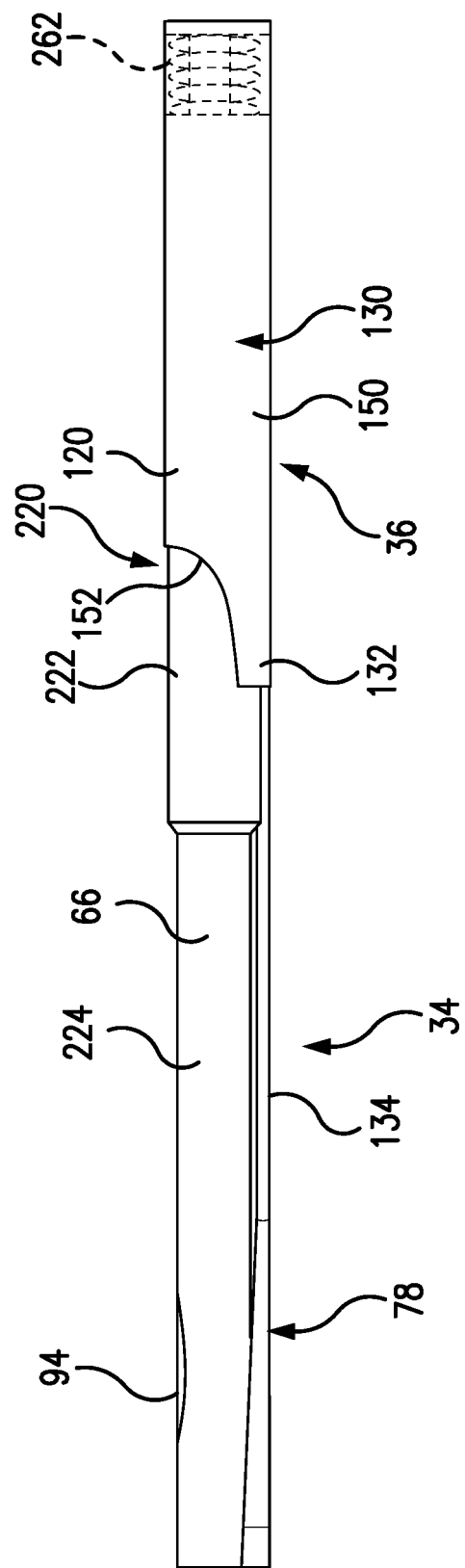

As shown in FIGS. 2A-2C, the subject guide catheter extension/pre-dilatation system 10 includes a balloon catheter sub-system 34 (also referred to herein as an inner catheter, inner member, or a pre-dilatation sub-assembly) and a guide catheter extension sub-system 36 (also referred to herein as an outer catheter). The inner catheter 34 interacts with the outer catheter 36 and can be engaged with or disengaged from the outer catheter 36, as required by the cardiac procedure.

The subject system 10 includes a proximal section 38, a distal section 40, and a middle section 42 extending between and interconnecting the proximal and distal sections 38, 40. A pre-dilatation balloon member 44 is carried at the distal section 40 of the inner catheter 34. The distal section 40 of the inner catheter 34 also may be configured with an elongated tapered micro-catheter 46, as will be detailed in the following paragraphs.

The subject guide extension/pre-dilatation system 10, as shown in FIG. 1, is extended within a lumen (internal channel) 48 of the guide catheter 14. In order to reliably reach the target location 22, and, in some cases, pass beyond the target location 22, the subject guide extension/pre-dilatation system 10, is advanced through the guide catheter 14 beyond a distal end 50 of the guide catheter 14 deep into the coronary artery 20. The subject system 10, by extending beyond the distal end 50 of the guide catheter 14, provides an adequate reachability of the pre-dilatation balloon 44 to the target location 22, and, by extending beyond the ostium 18 of the coronary artery 20, stabilizes the positioning of the guide catheter 14 and allows for an improved accessibility for the subject system 10 into the coronary artery 20 and to the target site 22.

As shown in FIGS. 1, 2A-2B, 3C-3D, 4, 5A-5C, and 6A, the guide wire 12 extends internal the guide catheter extension/pre-dilatation system 10, and exits the system 10 with the distal end of the GW 12 beyond the outermost end 52 of the distal section 40 and with the proximal end of the GW 12 at the middle section 42.

In operation, the inner catheter 34 and the outer catheter 36 are coupled one to another to be advanced (as a single unit) along the guide wire 12 inside the guide catheter 14 positioned within the blood vessel 16, and extend beyond the distal end 50 of the guide catheter 14 to reach the target lesion site 22. Once the subject balloon catheter sub-system (inner member) 34 reaches the lesion site 22, and the balloon member 44 is positioned in alignment with the lesion site 22, the intended pre-dilatation procedure may be performed. Once the pre-dilatation has been performed, the outer catheter (also referred to herein as outer member) 36 may be advanced across the lesion as an integral unit with the inner catheter (also referred to herein as an inner member) 34, with subsequent disengagement of the inner catheter 34 from the outer catheter 36 for withdrawal of the inner catheter from the outer catheter.

Alternatively, after the pre-dilatation procedure has been performed, the inner catheter 34 may be disengaged from the outer catheter 36, while the outer catheter 36 is advanced across the dilated lesion. In addition, the outer catheter 36 may be left in proximity to the lesion after the pre-dilatation has been performed and the inner catheter 34 has been removed.

In any case scenario, the outer member (catheter) 36 remaining in proximity to the pre-dilated lesion may be used for delivery of a stent inside the outer member (catheter) 36 to the lesion site. The outer member 36 is removed from the guide catheter 14 once the stent is installed (deployed) at the lesion site.

As will be presented in further paragraphs, in the subject system, the inner catheter 34 is prevented from forward displacement inside the outer catheter 36. Exclusively a backward or removal displacement of the inner member 34 relative to the outer member 36 is permitted to support retraction of the inner member from the outer member subsequent to the pre-dilatation of the lesion.

Referring to FIGS. 2A-2C, the proximal section 38 of the subject guide extension/pre-dilatation system 10 is represented by a balloon inflation hub 56 (best depicted in FIG. 2B) of the inner member 34 and a proximal end 58 of an outer member 36.

Referring to FIGS. 2B, 3A-3D, 4, and 5C, the inner member (also referred to herein intermittently as the balloon catheter sub-system or pre-dilatation balloon delivery subsystem) 34 is configured with an internal inflation channel 60 extending between the inflation hub 56 and the pre-dilatation balloon member 44. The internal inflation channel 60 serves as a passage for inflation air between a balloon inflation system 62 (shown schematically in FIG. 2B) and the balloon member 44 for the controlled inflation/deflation of the balloon member 44 as prescribed by the cardiac procedure.

The internal inflation channel 60 is formed by an inflation lumen hypo-tube 64 and an inflation lumen distal shaft 66 overlappingly interconnected each to the other in a fluidly sealed manner.

The inflation hub 56 located at the proximal end 68 of the inner member 34 is configured with an internal cone-shaped channel 70 which is connected by its proximal opening 72 to the balloon inflation system 62 (as schematically shown in FIG. 2B).

The balloon inflation system 62 may be a manual or an automatic system. In a preferred automatic embodiment, the balloon inflation system 62 includes an electronic sub-system, a pneumatic sub-system and control software with a corresponding user interface. The electronic sub-system, under control of the control software, supplies power to solenoid pressure valves (which are fluidly coupled to the balloon inflation hub 56) to control the pressurizing/depressurizing of the balloon member 44 with fluid or air flow.

As shown in FIG. 2B, the internal cone-shaped channel 70 of the balloon inflation hub 56 is configured with a distal opening 74 which is coupled to the inflation lumen hypo-tube 64. The proximal end of the inflation lumen hypo-tube 64 is coupled to the distal opening 74 of the internal cone-shaped channel 70 of the balloon inflation hub 56 in a fluidly sealed fashion to support passage of the inflation air between the balloon member 44 at the inflation system 62.

Figure 4:
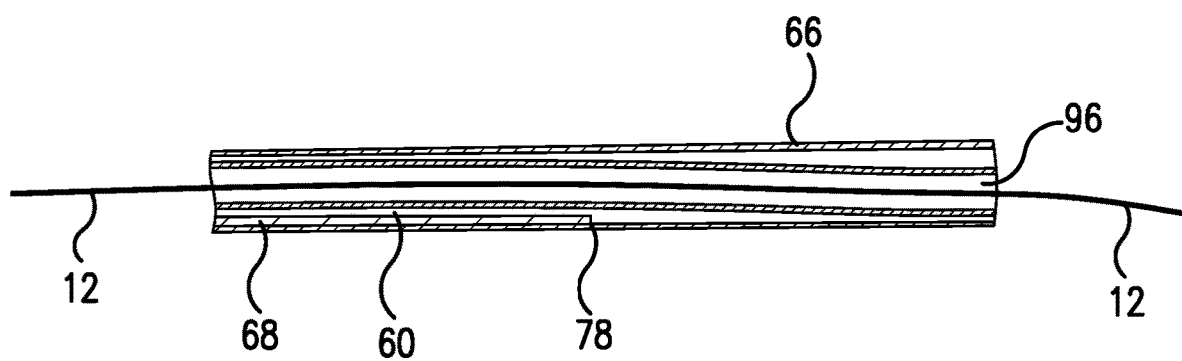
FIG. 4 shows a longitudinal section of the inner catheter detailing the distal end of the inflation hypo-tube at the junction with the inflation lumen distal shaft.

The inflation lumen hypo-tube 64 extends through the length of the proximal section 38 and a portion of the middle section 42 of the subject system 10 and terminates with its distal end 78 at the distal section 40, as shown in FIGS. 2B and 4.

As shown in FIG. 2B, a flexible serrated member 80 is provided at the proximal end 76 of the inflation lumen hypo-tube 64 which is coupled to the distal end 82 of the balloon inflation hub 56. The serrated flexible member 80 supports the proximal end 76 of the inflation lumen hypo-tube 64 and provides a flexible bending of the structure when manipulated by a surgeon.

Figure 3A:
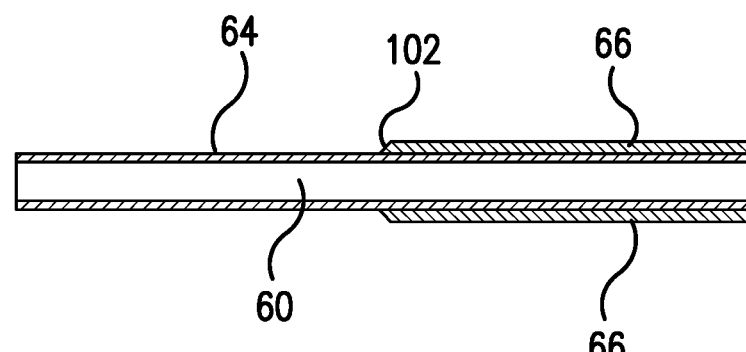
FIG. 3A-3D are representative of the middle section of the subject inner catheter with FIG. 3A showing a longitudinal section of the inflation lumen hypo-tube interconnected with the inflation lumen distal shaft in the inner catheter, FIG. 3B detailing a longitudinal section of the skived portion of the inflation lumen hypo-tube, FIG. 3C showing a longitudinal section of the inner catheter depicting an RX guide wire (GW) port formed in the inflation lumen distal shaft, and FIG. 3D showing an isometric view of the RX port portion of the inner catheter shown in FIG. 3C.

As shown in FIGS. 2A-2C, 3A-3D, 4 and 5C, the inflation lumen distal shaft 66 extends between the proximal section 38 along the middle section 42 and ends at the distal section 40. FIG. 3A details the junction between the inflation lumen hypo-tube 64 and the inflation lumen distal shaft 66. The inflation lumen hypo-tube 64 does not extend all the way through the inner member 34 but terminates at its distal end 78 (as shown in FIGS. 2B and 4).

Figure 3B:
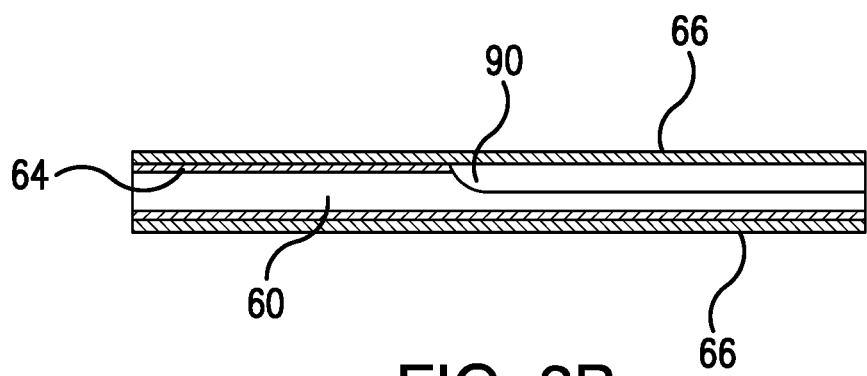
Figure 3C:
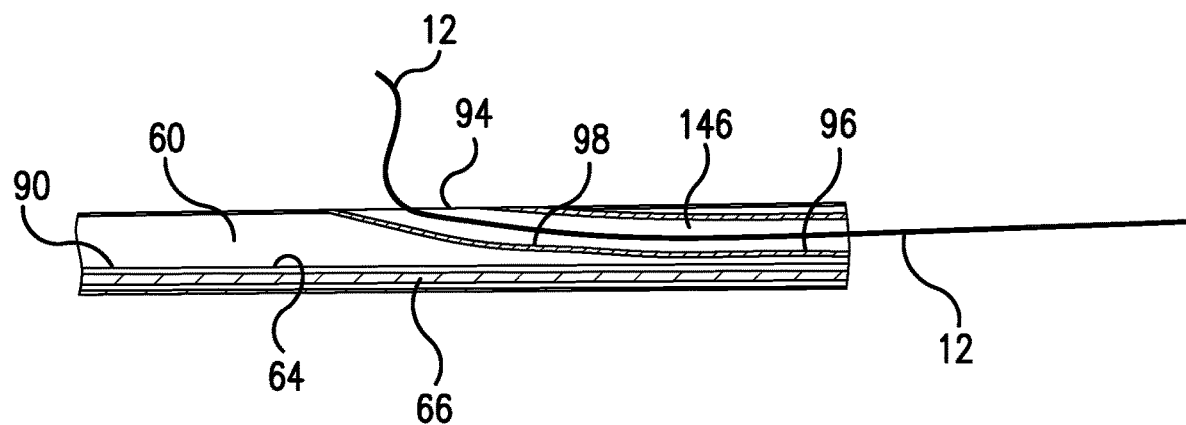
Figure 3D:
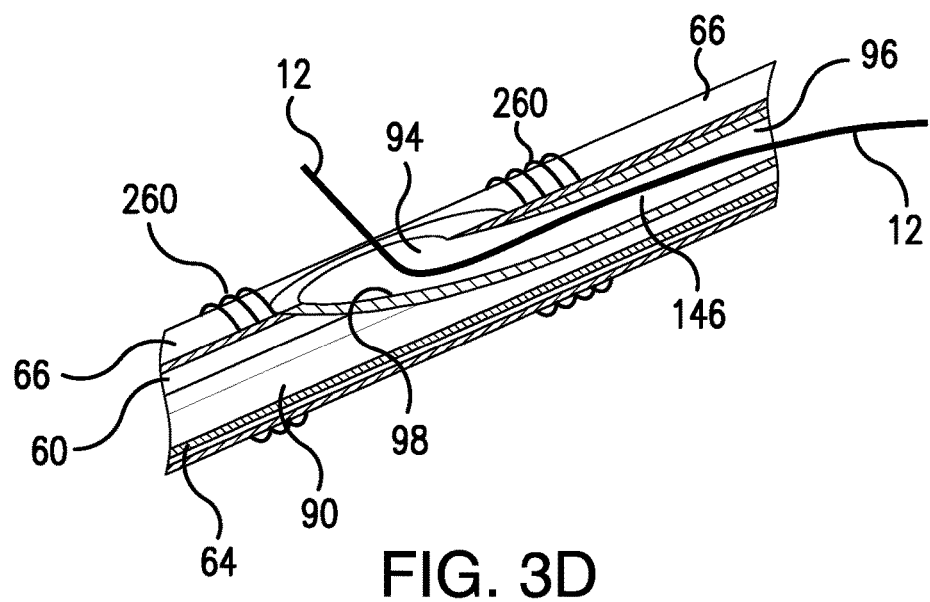
Figure 5A:
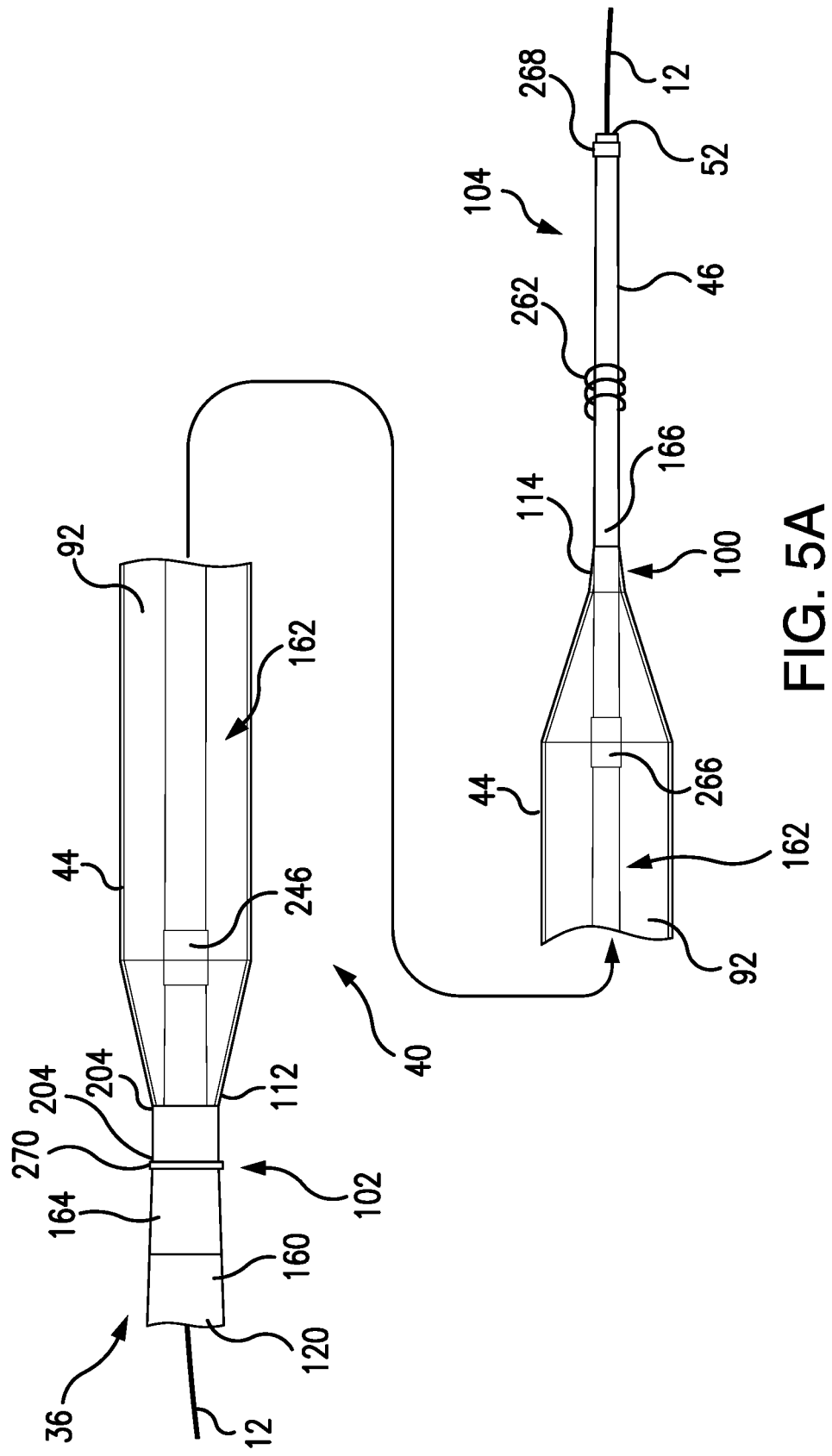
Figure 5B:
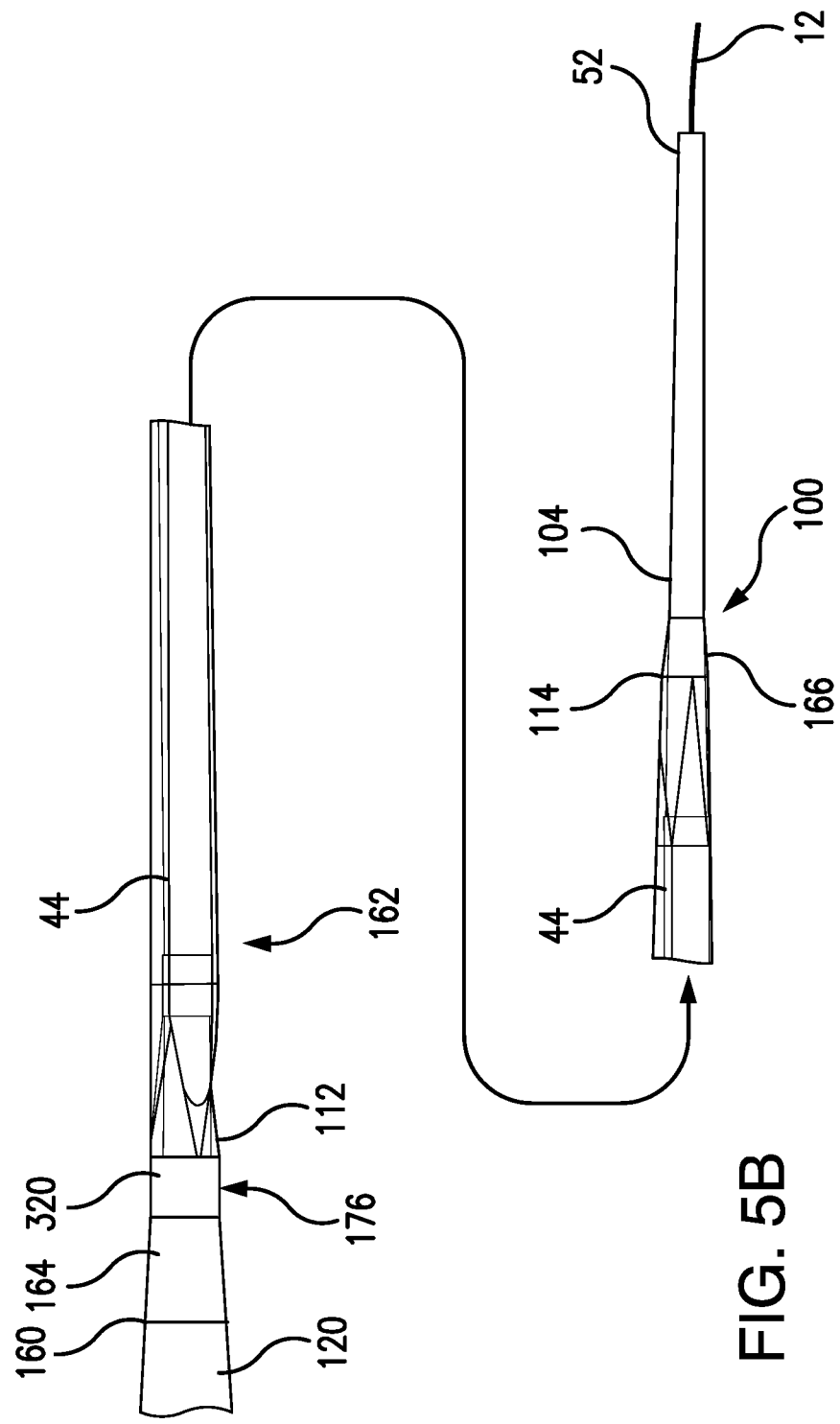

Referring to FIGS. 3B-3D, the inflation lumen hypo-tube 64 has a skived distal portion 90 which is coaxially enveloped by the wall of the inflation lumen distal shaft 66 so that the inflation lumen hypo-tube 64, in conjunction with the inflation lumen distal shaft 66, provide a sealed fluid communication between the balloon inflation system 62 and the internal chamber 92 of the balloon member 44, as shown in FIGS. 5A-5C, for controlled inflation/deflation of the balloon member 44 as required by the cardiac procedure.

FIGS. 2B and 3C-3D illustrate that the inflation lumen distal shaft 66 is configured with a rapid exchange (RX) guidewire (GW) port 94 at which a GW lumen 96 begins with its proximal end 98. The GW lumen 96 extends between the RX GW port 94 inside the inflation lumen distal shaft 66 through the entire length of the distal section 40 of the inner catheter 34. The GW lumen 96 forms an internal channel with the proximal end 98 corresponding to the RX GW port 94 and a distal end 100 corresponding to the outermost distal end 52 of the distal section 40 of the inner member 34. As shown in FIGS. 6A-6B, at the distal section 40, the GW lumen 96 extends beyond the distal end 102 of the inflation lumen distal shaft 66. The distal end 100 of the GW lumen 96 constitutes a gradually tapered portion 104 which may be in the form of a delivery micro-catheter 46.

Referring to FIGS. 2A-2B, 5A-5C, 6A-6B, and 24A-24B, the inner catheter (also referred to herein as a balloon catheter sub-system) 34 is configured with a tapered distal portion (also intermittently referred to herein as tapered distal tip) 162 at the distal section 40. The tapered distal portion 162 is equipped with the pre-dilatation balloon member 44 which is secured onto the tapered distal portion 162 in close proximity to the micro-catheter 46. The pre-dilatation balloon member 44 is secured to the inner member's tapered distal portion (tip) 162 for supporting the pre-dilatation/stenting procedure, as required for the cardiac treatment of a patient.

The balloon member 44 has a proximal portion 112 and a distal portion 114. The balloon member 44 is attached (secured) at the distal section 40 in proximity to the delivery micro-catheter 46 with its proximal portion 112 coupled to the distal end 102 of the inflation lumen distal shaft 66, and with the distal portion 114 of the balloon 44 to the outer surface of the micro-catheter 46.

As shown in FIGS. 5A-5C, the pre-dilatation balloon 44 is attached, with its proximal portion 112, to the proximal portion 204 of the distal tip 162 in bordering juxtaposition with the outer tip 164 of the sheath 120, and, with its distal portion 114, to the distal end 166 of the distal portion (tip) 162 of the inner member 34.

The balloon member 44 may intermittently assume deflated (folded) and inflated (expanded) configurations. The deflated (folded) configuration is used during insertion and/or withdrawal of the subject system relative to the blood vessel. The balloon is inflated (expanded) when in place (at the target site 22) to widen the blood vessel and compress the plaque for pre-dilatation procedure, or for the stenting procedure (when a stent is delivered to the treatment site on a balloon). When inflated, the balloon 44 assumes the inflated/open configuration shown in FIGS. 2A-2B, 5A, 5C, 6A-6B, and 24A-24B for pre-dilatation of the diseased blood vessel. When deflated, the balloon member 44 assumes the deflated configuration shown in FIG. 5B.

The balloon 44 may have a smooth surface, or a "chocolate" configuration. The "chocolate" balloon catheter is an over-the-wire balloon dilatation catheter with a braided shaft and an atraumatic tapered tip. The balloon, when expanded, is constrained by a nitinol structure that creates small "pillows" and grooves in the balloon.

Referring now to FIGS. 2A, 2C, 5A-5C, 7, 8A-8B 9A, 9C-9D, 10A-10G, 11C, 12B-12C, 13A-13B, 14B, 15A-15D, 16A-16B, 17A-17B, 18A-18B, 19B, 20A-20B, 21, and 24A-24B, the outer catheter (also referred to as the guide catheter extension sub-system) 36 is formed with a cylindrical outer delivery sheath 120 having an internal channel 122 extending internally therealong. A coupler mechanism 130 is formed at the proximal end 132 of the cylindrical sheath 120 in encircling relationship therewith.

At the proximal end 58, the outer catheter 36 includes an outer member pusher (also referred to herein as a pusher/puller) 134, which, as shown in FIGS. 10B-10G, 11A-11C, 12A-12C, 13A-13B, 14A-14B, 15A-15D, 16A-16B, 17A-17B, 18A-18B, 19B, and 22, in one embodiment, may be a solid wire which may have a round wire proximal section 136, and a flattened distal portion 138 which may be welded or otherwise fixedly attached to the proximal end 132 of the sheath 130. In another embodiment, the pushing and pulling element 134 may be configured with a hypo-tube.

Alternatively, a round pusher wire can be welded to a flat wire which, in its turn, is welded or otherwise fixedly secured to the proximal end 132 of the sheath 120.

In still another alternative embodiment of the outer member 36, a round wire may be welded or otherwise fixedly secured to two flat wires, which in their turn, are welded or otherwise fixedly secured to the proximal end 132 of the sheath 120.

The flattened profile of the pusher wire portion is welded to the proximal coupler 130 of the outer sheath 120 so that when the inner member 34 is inserted in the outer member (catheter) 36, the pusher wire does not create an obstacle for the rotational or longitudinal motion of the inner catheter 34 inside the proximal coupler 130 and the sheath 120 of the outer member 36, as required by the procedure. The proximal pushing-pulling element 134 advances with or withdraws the outer tubular sheath 120 and is preferably flexible (not rigid). The pusher/puller 134 may be flexible (not rigid) with the flexibility along its longitudinal axis being comparable or exceeding the flexibility of the tubular outer delivery sheath 120 of the outer catheter 36.

The outer catheter's pusher 134 may be equipped, at the proximal end thereof, with a proximal handle 140, shown in FIG. 10F, for convenience of a surgeon performing the coronary intervention procedure for manipulation of the outer member 36 in order to position the outer delivery sheath 120 along with the balloon delivery sub-system 34, at the desired location relative to the lesion 22 in the diseased blood vessel.

The proximal (wire or hypo-tube configured) pushing/pulling element 134 connected to the outer member's tubular structure 120, by having a miniature profile and being flexible (not "rigid"), attains an enhanced conformability inside the guiding catheter and a lower profile than the rigid "pushing" elements in conventional guide extension catheters (as per Root). This is made possible due to the "pushability" of the "system as a whole", attained via the locked integral connection between the outer catheter (with its hypo-tube pushing element) and the inner catheter (guide extension tube).

In addition, the inner catheter (inner member) 34 may be equipped with an inner member's pusher (also referred to herein as a pusher/puller) 142 (shown in FIG. 2A) which may be attached to the inflation hub 56 to facilitate the withdrawal of the inner member 34 from the outer member 36 as required by the coronary intervention procedure, as well as for controlling engagement/disengagement therebetween, for various stages of the cardiac procedure. The inner member's pusher/puller 142 may be formed with an inner member pusher/puller's handle for convenience of a surgeon performing the procedure.

The handles of the inner and outer members' pushers may be configured with a mechanism (detailed in the U.S. patent application Ser. No. 15/899,603 which is hereby incorporated by reference) which permits an additional releasable locking of the inner and outer members one to the other to enhance the integral cooperation thereof in an engaged mode of operation.

The inner member 34 may be either of the over-the-wire configuration or of the RX configuration. In one of the embodiments detailed herein, the guide wire 12 extends through the RX GW port 94 made at the proximal end of the tubular inflation lumen distal shaft 66 into and along the internal channel 146 of the GW lumen 96, as shown in FIGS. 3C-3D, and 4. At the distal section 40 of the subject system 10, the guidewire 12 extends in the GW lumen along the delivery tapered micro-catheter 46 (at the tapered portion 104), and exits at the distal ends 100 of the GW lumen 96 at the outermost end 52 of the inner member 34, as shown in FIGS. 2A-2B, 5A-5B, and 6A-6B.

The outer delivery sheath 120 of the outer member 36 is fabricated with a flexible cylindrically shaped tubular body 150 extending substantially the length of the middle section 42 of the subject system 10. By manipulating the outer member pusher 134, a surgeon actuates the integral advancement of the outer delivery sheath 120 and the inner member 34 along the guide catheter 14. When the pre-dilatation procedure has been performed (as will be detailed in further paragraphs), the surgeon controls a required linear backward displacement of the inner member 34 with regard to the sheath 120 of the outer member 36 by manipulating the outer member pusher 134 and/or the inner member pusher 142.

The interface between the outer tip 164 of the sheath 120 and the distal tip 162 of the inner member 34, as shown in FIGS. 8A-8B and 9A-9D, facilitates displacement of the distal tip 162 of the inner member 34 relative to the outer tip 164 of the sheath 120 and basically facilitates displacement of the distal tip 162 relative to the outer tip 164 of the sheath 120 as required by the cardiac procedure.

The distal end 160, as well as the outer tip 164 of the sheath 120, is formed of a flexible material which permits a simplified retraction of the distal tip 162 of the inner member 34 therethrough. The flat wire helical coil may be used for the distal end 160 and the outer tip 164 of the sheath 120.

At its proximal end 132, the sheath 120 of the outer catheter 36, is configured with an entrance "opening" (or a "mouth") 210 the circumference of which exceeds the circumference of the outer member flexible tubular sheath 120, as shown in FIGS. 10A-10G. The entrance 210 (also referred to herein as a "mouth") into the internal channel 122 of the sheath 120 may be configured in various modifications. For example, as shown in FIG. 10A, the entrance 210 has a funnel shape 211 with an eccentric opening (as shown in FIG. 10A), or contoured with a concentric blunt (as shown in FIGS. 10B-10C), or with a concentric bevel (as shown in FIGS. 10D-10E), or alternatively, with the concentric concave contour (as shown in FIGS. 10F-10G). The pusher 134 is affixed at a predetermined point of the funnel shape outer catheter's proximal entry 210.

As shown in FIGS. 2A, 2C, 7, and 8A-8B, the outer delivery sheath 120 of the outer catheter 36 extends between its proximal end 132 at the middle section 42 and its distal end 160 at the distal section 40 of the subject system 10. At the distal section 40 of the subject guide catheter extension/pre-dilatation system 10, the inner member 34 is configured with a tapered configuration 104 having a distal tapered portion (also referred to herein as a distal tapered tip) 162 which may be formed with the micro-catheter 46, as shown in FIGS. 2A-2B, 5A-5B, 6A-6B, 8A, 22A-22B, and 24A-24B. The micro-catheter 46 is an elongated thin member with the length in a cm range, for example, 1-3 cm. The micro-catheter 46 has a tapered cone-contoured configuration with the diameter not exceeding 1 mm at its distal end 52. The micro-catheter 46 may be formed integrally with the tapered distal tip 162 of the inner member 34.

As shown in FIGS. 2A, 5A-5C, 7, and 8A-8B, at the distal end 160, the outer delivery sheath 120 is formed with an outer tip 164 which has a tapered cone-contoured configuration which may be interconnected with the distal tip 162 of the inner member 34. The outer tip 164 of the outer member 36 provides a smooth distal taper transition between the distal end 160 of the sheath 120 and the distal section 40.

In FIGS. 2A, 5A-5B, 6A-6B, 8A-8B, 22A-22B, and 24A-24B, the distal tip 162 of the inner catheter 34 is shown to have a tapered configuration which changes gradually from the point of interconnection with the outer tip 164 of the sheath 120 to the distal end 166 of the distal tip 162. The micro-catheter 46 extends from the distal end 166 of the distal tapered portion 162 of the inner member 34 (the length of about 1-3 cm) in an integral connection therewith and terminates in the outermost distal end 52.

The subject guide catheter extension/pre-dilatation system 10 may be configured with a differential in micro-catheter flexibility with greater flexibility in the distal portion, by either changing the durometer of the plastic (polymeric) components from the outer delivery sheath's proximal portion to its distal portion (i.e., a higher durometer in the proximal portion when taken with respect to the distal portion), and/or changing the winding frequency (pitch) of the helical coil of wire in the micro-catheter 46 in the direction from the proximal portion to distal portion, such that the distal portion of the micro-catheter 46 is more flexible and trackable than the proximal portion of the micro-catheter delivery device, with a substantially lower profile and is more flexible than the distal portion of the guide catheter extension sub-system (outer delivery sheath).

The system 10 may also include wires that have radio-opacity such that the balloon member 44, micro-catheter 46, and the outer delivery sheath 120 are easily visualized using fluoroscopy. It is envisioned that the distal tip 162 (as shown in FIGS. 5A, 6A-6B) is provided with radio-opaque markers 264, 266 in proximity to the proximal portion 112 and the distal portion 114 of the balloon 44. The radio-markers 264, 266 permit the surgeon (operator) to visualize positioning of the balloon member 44 relative to the lesion location 22.

In addition, the outermost distal tip 52 of the micro-catheter delivery portion 46 and the tip 160 of the sheath 120 may have one or more radio-opaque markers 268, 270 (shown in FIGS. 2B and 5A) in order to permit the surgeon to distinguish between the radio-markers, which is particularly important as the obstructive lesion is passed by the micro-catheter, and the balloon member carried in proximity to the micro-catheter is held in place.

Figure 7:
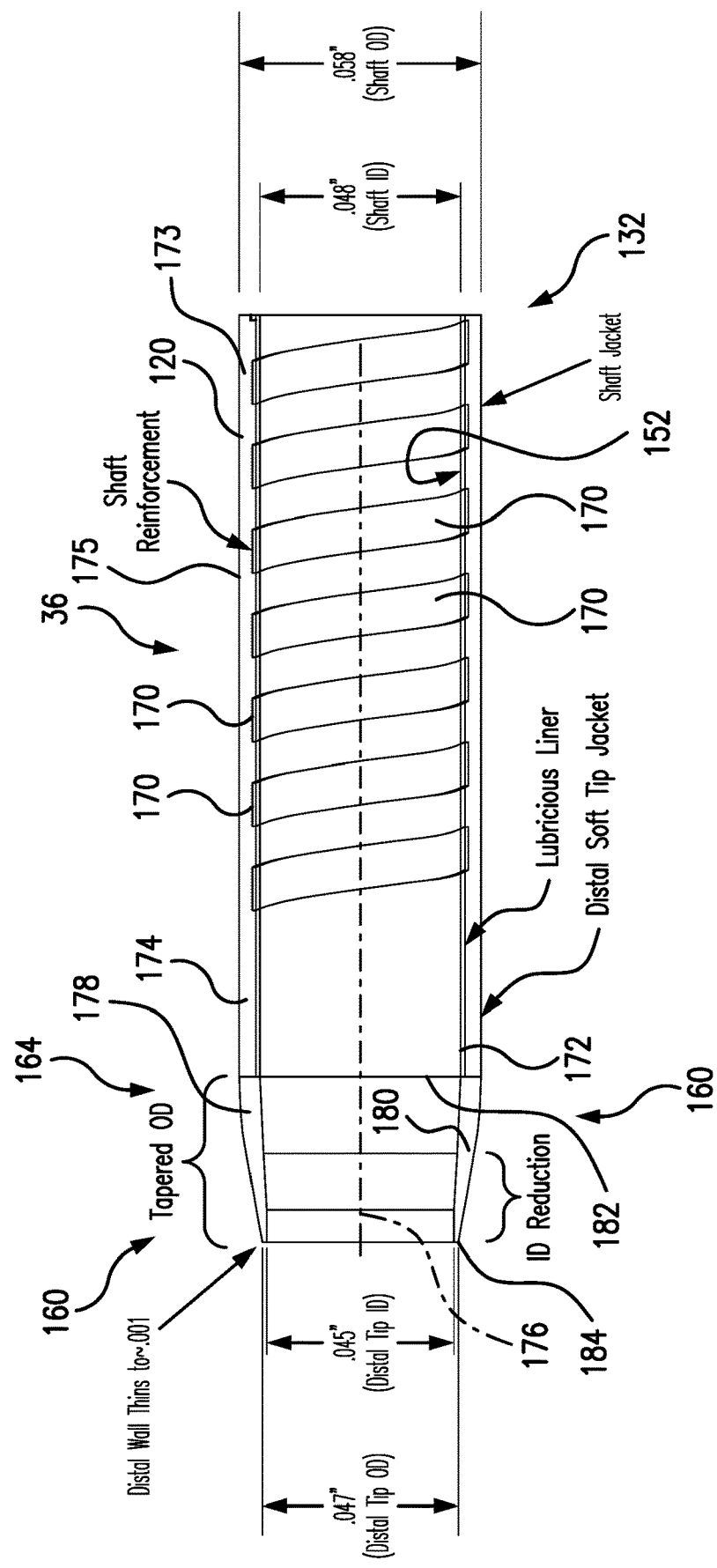
FIG. 7 depicts the distal tip of the outer catheter.

As detailed in FIG. 7, in one embodiment thereof, the outer catheter 36 is configured with a system of catheter shaft coil reinforcement 170 disposed on (or embedded in) the internal surface 152 of the sheath 120. Preferably, a lubricious liner 172 is positioned inside the shaft 120. The shaft reinforcement coil 170 may be installed inside the shaft 120 in contact with the lubricious liner 172, i.e., in encircling relationship with the surface of a lubricious liner 172 which covers the inner surface 152 of the shaft 120. A distal soft tip jacket 174 is affixed at the distal end of the outer catheter shaft 120 along the longitudinal axis 176 of the outer catheter 36.

The distal soft tip jacket 174 may be glued to the shaft 120 at the end 175 (as shown in FIG. 7), or may cover some length of the outer surface 173 of the shaft 120.

The distal soft tip jacket 174 extends at the distal end 160 of the shaft 120 beyond the coil reinforcement 170 and the lubricious liner 172, and terminates in the tapered portion 178, which has a distal edge 184 and a proximal edge 182.

The lubricious liner 172 may be formed from the PTFE material. The distal soft tip jacket 172 may be formed of a very flexible low durometer elastomeric Pebax material which transitions into high durometers along the longitudinal axis 176 towards the proximal end 132 of the sheath 120.

Figure 8A:
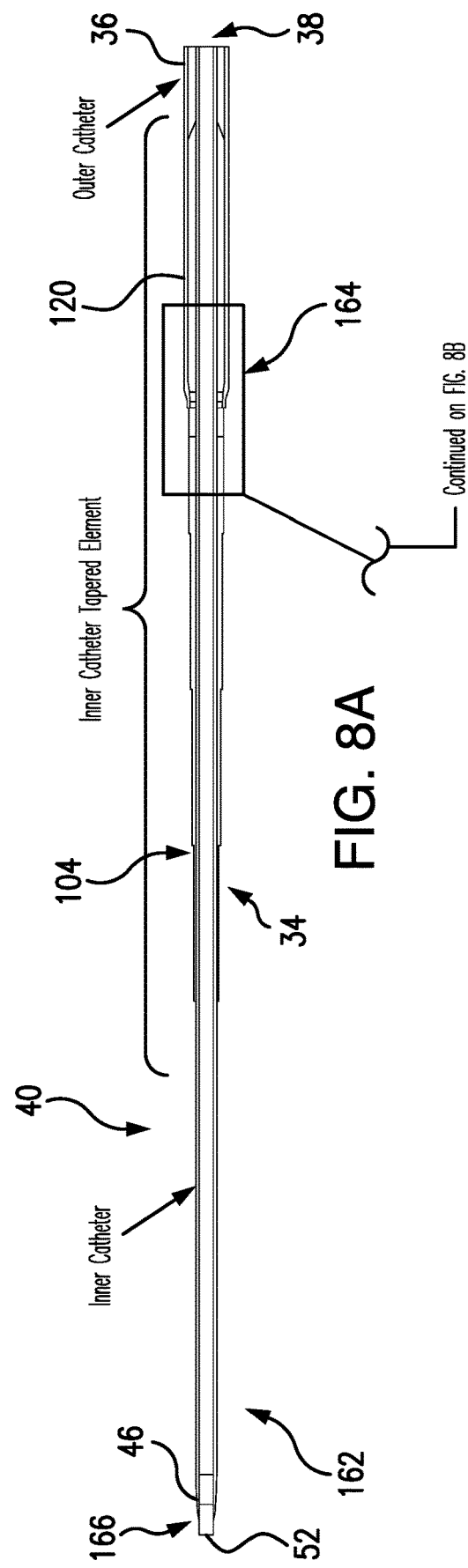

As shown in FIGS. 7 and 8A-8B, in one of the preferred embodiments, the internal diameter of the sheath 120 at its inner surface 152 is approximately 0.048", while the outer diameter of the shaft 120 at its outer surface 173 is 0.058". The internal diameter of the tapered portion 178 of the outer catheter 36 at the distal edge 184 is 0.045", while the outer diameter of the tapered portion 178 at its distal edge 184 is 0.047". The gradient between the outer diameter (0.058") of the sheath 120 and the outer diameter of the taper 178 (0.047") define the outer surface tapering, while the gradient between the inner diameter (0.048") of the sheath 120 at the inner diameter (0.045") of the taper 178 at its distal edge 184 define the tapering of its inner surface. The distal wall 180 of the tapered portion 178 has a thickness reduction from the interface 182 (between the sheath 120 and the tapered portion 178) to the outermost edge 184 of the tapered portion 178 of the distal soft tip jacket 174.

As shown in FIG. 7 in conjunction with FIGS. 8A-8B, the outer diameter of the inner catheter's tapered element 104 has the outer diameter approximately 0.046" which is approximately 0.001" larger than the outer catheter's distal tip internal diameter (0.045") at the outermost distal edge 184. This difference between the outer diameter of the tapered element 104 of the inner catheter 34 and the inner diameter at the distal edge 184 of the outer catheter's outer tip 164 results in stretching of the distal soft tip jacket 174 at the tapered portion 178 thereof when interfering with the inner catheter's tapered element 104. Such arrangement provides for a near seamless transition between the distal tip of the inner catheter 34 and the distal tip of the outer catheter 36, as well as a miniature profile of the distal end due to the squeezing of the distal tip of the inner catheter 34 by the tapered element 178 of the outer catheter 36. Upon removal of the inner catheter 34, the distal tip of the elastomeric properties of the distal soft tip jacket 174 of the outer catheter 36 permit the tapered portion 178 to return to its original internal diameter (0.045").

In the disengaged mode of operation, said inner diameter of the wall 180 of the tapered outer tip 164 of the outer member 36 is smaller than the outer diameter of the inner member 34. In the engaged mode of operation, the tapered outer tip 164 of the outer member 36 and the inner member 34 interact such that a dimensional transition between the outer diameter of the tapered outer tip 164 of the sheath lumen 120 and the outer diameter of the distal portion of the inner member 34 forms a substantially flush interface transition therebetween.

Figure 9A:
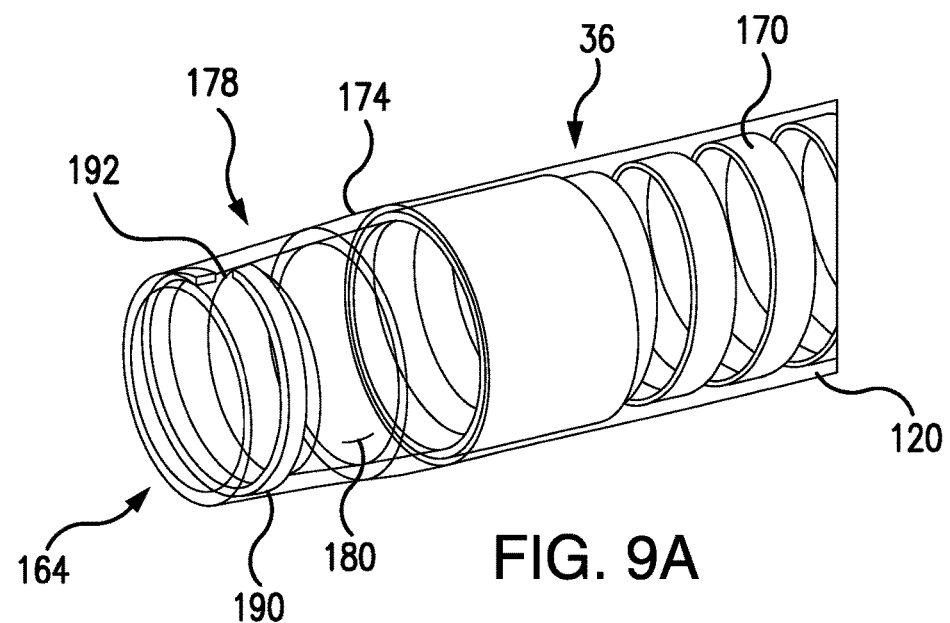
FIGS. 9A-9D are representative of alternative embodiments of the elastically stretchable distal tip of the outer catheter configured with an expandable split ring (FIG. 9A), expandable tip scaffold (FIG. 9B), and slits (FIGS. 9C-9D)

Referring further to FIGS. 9A-9D, the tapered portion 178 is contemplated in several embodiments of the expandable tapered designs. As shown in FIG. 9A, the elasticity of the outer catheter 36 at its distal tapered portion 178 is augmented by an expandable split ring 190 affixed at the tapered portion 178 which allows the distal outer tip 164 to expand (when interfaced with the inner catheter 34). The expandable split ring 190 has a slit 192 which allows the ring 190 to expand and contract, depending on the interference between the inner and outer catheters at their distal ends. This structure provides an additional reinforcement to prevent a permanent deformation of the tapered portion 178 during the inner catheter 34 removal and delivery of the stent (or the balloon).

Figure 9B:
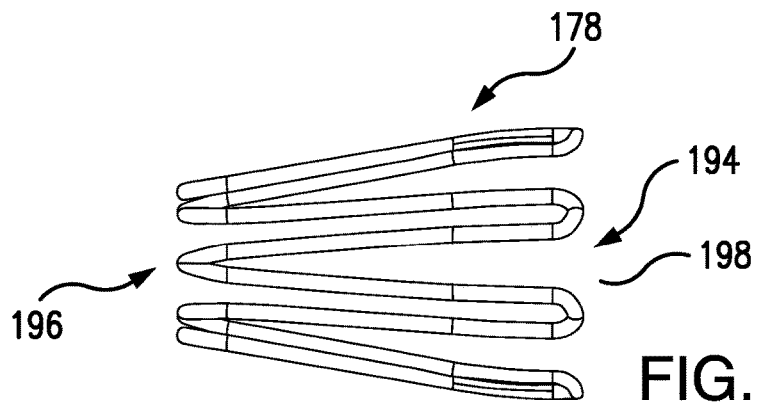

Referring to FIG. 9B, in an alternative embodiment of the outer catheter 36, the tapered portion 178 may be configured with an expandable tip scaffold 194 which may be fabricated from NiTi wire and configured with a distal end 196 and a proximal end 198 which has a diameter larger than the diameter of the distal end 196. Due to its flexibility, the expandable scaffold 194, expands and contracts, when needed, and provides additional support to resist a permanent deformation of the jacket 174 at the tapered portion 178 during the inner catheter removal and delivery of the stent or the balloon member.

Figure 9C:
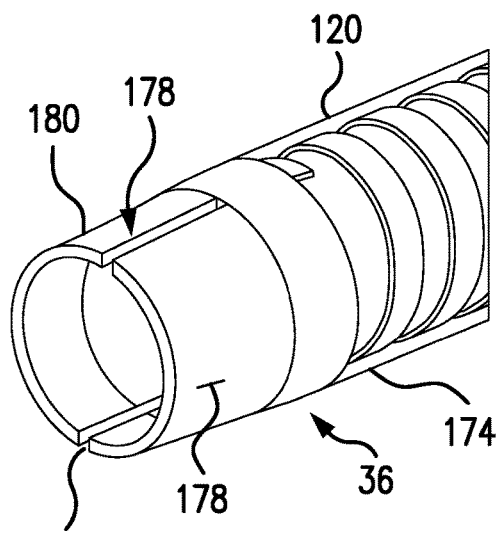
Figure 9D:
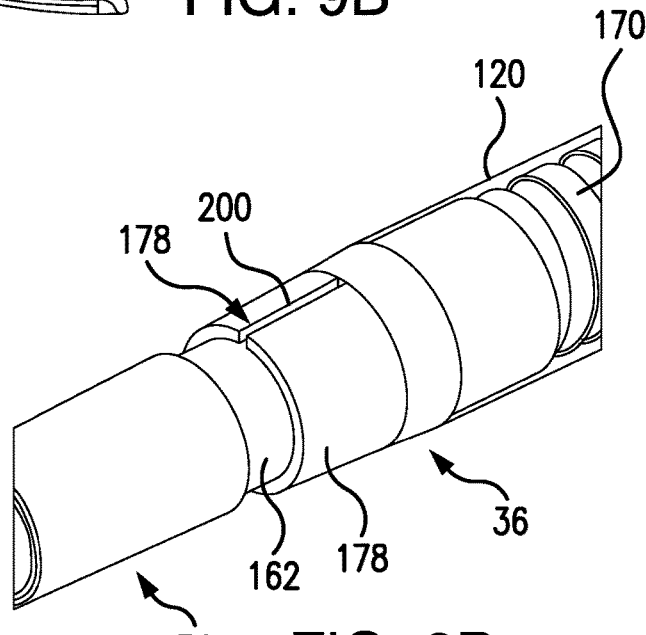

Another alternative embodiment of the tapered portion 178 at the distal end of the sheath 120 is shown in FIGS. 9C-9D, where wall 180 of the tapered portion 178 is shaped with slits 200 which extend longitudinally along the length of the tapered portion 178 spread apart along its perimeter. When the tapered portion 178 interfaces with the distal end of the inner member 34, the slits 200 temporarily widen to embrace the distal tip 162 of the inner catheter 34. This design can prevent a permanent deformation of the jacket 174 at its tapered portion 178 which may be caused by the inner catheter 34 removal or during the stent/balloon number delivery.

An important "seamless" aspect of the subject system is that for a transition between the outer diameter of the outer tip 164 of the sheath 120 (at the tapered portion 178 thereof) and the outer diameter of the distal tip 162 of the inner member 34 forms substantially gradual (smooth) transition therebetween.

As shown in FIGS. 2C, 10A-10G, 11A-11C, 12A-12C, 13A-13B, 14A-14B, and 15A-15D, the subject system is built, at the middle section 42, with an interconnection mechanism 220 which includes the proximal coupler 130 formed at the proximal end 132 of the sheath 120 of the outer member 36, and a cooperating mechanism 222 formed at the outer surface of the inner member 34 (as depicted in FIGS. 17A-17B, 18B, 19A-19B, and 20A-20C).

The subject guide catheter extension/pre-dilatation system 10 may operate in an inner/outer catheters engagement mode and in an inner/outer catheters disengagement mode, which is accomplished by controlling the interconnection mechanism 220. The subject interconnection mechanism 220 is configured to engage/disengage the inner and outer catheters 34, 36 (as required by the cardiac procedure), as well as to prevent an unwanted forward displacement of the inner member 34 inside the outer delivery sheath 120. The engagement mode of operation allows the enhanced "pushability" of the "system as a whole" (with the outer catheter 36 connected and locked to the inner catheter 34) even with the connected pushing/pulling element 134 of the outer member 36 configured as a low profile and flexible element (as flexible or more flexible than the outer tubular sheath 120 of the outer catheter 36).

The interconnection unit 220 operates based on the interference between the proximal coupler 130 configured at the proximal end 132 of the sheath 120 and the cooperating mechanism 222 configured at the outer surface 224 of the inner member 34 when the inner surface 152 of the tubular body 150 of the sheath 120 (at its proximal end 132) engages the outer surface 224 of the cooperating mechanism 222 (on the inner member 34).

As an example, a number of interconnection mechanisms are envisioned to be applicable in the subject guide catheter extension/pre-dilatation system 10. The subject engagement mechanism is configured for controllable engagement/disengagement between the inner member 34 and the outer member 36, as well as to prevent a forward motion of the inner member 34 relative the outer delivery sheath 120 beyond a predetermined position.

For example, as depicted in FIGS. 11A-11C, a laser cut coupler 130 may be configured with a proximal open (split) ring 240 and a pair of distal rings including a solid distal ring 242 and an open (split) distal ring 244. The proximal open ring 240, as well as the distal rings 242 and 244, is formed integrally with a coupler base 246. The coupler 130 may be formed from stainless steel or heat set NiTi. The pusher/puller element 134 of the outer catheter 36 and the mid-shift coupler (also referred to herein as a proximal coupler) 130 may be made from a memory metal (such as, for example, nitinol) so as to prevent deformation during antegrade or retrograde movement of the outer member and to prevent any deformation of the mid shaft coupler 130 during the stent (or other device) passage through the mid shaft portion of the outer catheter 36.

The open ring 240 is correlated with the proximal entry opening, (for example funnel shaped) 211 of the outer catheter 36 (shown in FIGS. 10A, 10D-10E and 11C). The proximal open ring 240 allows for expansion of the entrance 211 into the funnel 210 as needed for entrance/removal of the inner catheter 34 as required by the surgical procedure. As shown in FIGS. 10A, 10D-10E, and 11A-11C, the proximal open ring 240 provides a support for the proximal opening 210 of the funnel shaped proximal end of the sheet 120. The proximal ring 240 reinforces the entrance opening ("mouth") 211 and prevents from the damage or a permanent deformation of the entrance opening, thus supporting elastic properties of the sheath 120 at the entrance opening 210. The distal rings 242, 244 create a snap-fit lock mechanism separate from the funnel's proximal open ring 240. The distal ring 242 is not expanded (being of a closed circular contour), while the opening of the split ring 244 expands during the displacement of the inner catheter 34 relative to the proximal coupler 130 of the outer catheter 36.

The base 246 of the coupler 130, as shown in FIGS. 11B-11C, may be flat, or preferably, is slightly arcuated (in the cross-section) to be congruent with the cooperating distal end 250 of the pusher 134 which has either flat or crescent (in crossing direction) contour. The pusher 134 may be fabricated from stainless steel or NiTi. The distal end 250 of the pusher 134 is welded (glued, adhered or otherwise affixed) to the base member 246 of the coupler 130. The PTFE liner (also shown in FIG. 7) 172 may encapsulate the coupler 130 as shown in FIG. 11C.

The sheath 120 is positioned in surrounding relationship with the coupler and the PTFE liner 172. The Pebax encapsulation, similar to the distal soft tip jacket 174, at the distal end 160 of the sheath 120 (shown in FIG. 7) may be used at the proximal end 132 of the sheath 120. The catheter shaft coil reinforcement 170 (also shown in FIG. 7) at the distal end of the outer catheter 36 can extend the length thereof to the proximal end of the outer catheter 36.

As shown in FIGS. 11A-11C, and 17A-17C, and 18A-18B, cooperating mechanism 222 for the specific embodiment shown in FIGS. 11A-11C further includes a mid-shaft lock ring 252 (shown in FIGS. 17B-17C and 18B) for the snap-fit locking.

Another embodiment of the outer catheter's proximal entry structure shown in FIGS. 12A-12C, is similar to the one shown in FIGS. 11A-11C with certain modifications, including:
(a) an added thickness and additional material around the base 246 of the coupler 130;
(b) modified surface treatment (e.g., bead blasting) for improving the polymer encapsulation adhesion; and
(c) using the hard polymer (such as Nylon) encapsulation to provide additional support to the funnel to prevent damage which may impede the stent passage.

An additional embodiment of the coupler 130 at the proximal entry 210 (shown in FIGS. 13A-13B) features open rings (ribs) 256 which reinforce the entrance port 210. The snap-fit lock 260 is represented by at least two open rings 262 at the distal end of the coupler 130. The coupler 130, as shown in the modification presented in FIGS. 13A-13B, is preferably a laser cut coupler formed either from a stainless steel or heat set NiTi.

The hypo-tube pusher/puller 134 may be flattened at its distal end 250 and is welded to the base 246 of the coupler 130. The PTFE liner 172 extends underneath the coupler 130, and the Pebax encapsulation 174 envelopes the coupler 130 with the pusher 134 affixed thereto. The catheter shaft coil reinforcement structure 170 extends along the shaft 120 of the outer catheter 36 from the distal to the proximal end thereof. The snap-fit lock 260 cooperates with the round ring embodiment of the cooperating mechanism 222 shown in FIGS. 17A-17C and 18B. In some embodiments, the encapsulation 174 and/or the pusher/puller 134 may be color coated with a distinct color, as shown in FIG. 11A, to distinguish the outer member's pusher/puller 134 from other elements of the subject arrangement for the surgeon convenience and safety of the procedure.

Figures 14A, 14B:
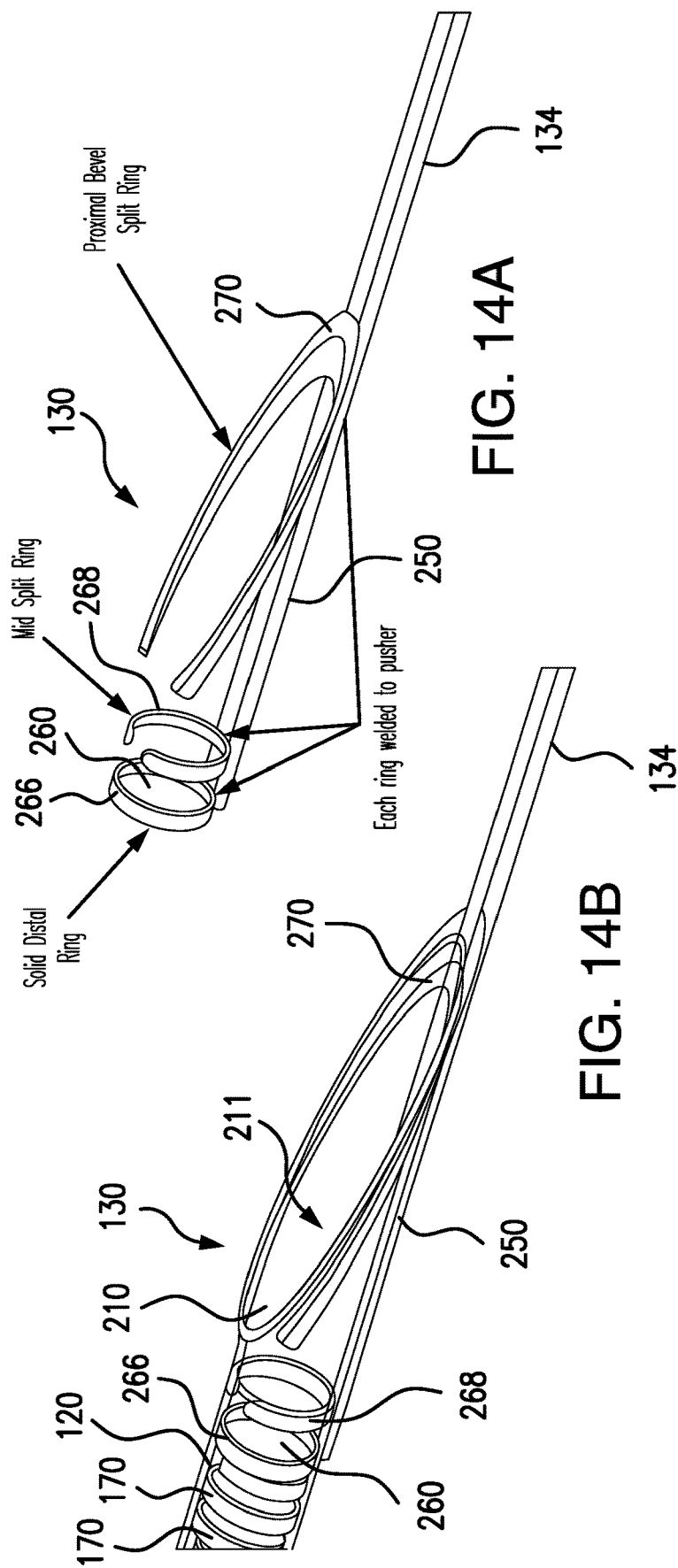
FIGS. 14A-14B depict welded rings embodiment of the proximal entry of the outer catheter, with FIG. 14A showing the welded rings coupler, and FIG. 14B showing the encapsulated welded rings coupler.

An additional modification of the coupler 130 is presented in FIGS. 14A-14B where the coupler 130 has individual rings 266, 268 welded to the distal end 250 of the pusher 134. As shown, the locking mechanism 260 is formed by the solid distal ring 266, and the mid split ring 268, with each ring 266, 268 welded to the pusher 134. The proximal bevel split ring 270 is also welded to the pusher 134. This design offers an increased flexibility in terms of the size and configuration of each ring 266, 268 and 270, and supports the formation of different funnel shapes/dimensions, as opposed to the laser cut coupler limited to a single diameter.

FIGS. 15A-15B depict another modification of the proximal coupler 130 which features funnel fenestrations which improve the contrast infusion flow rate by providing an additional open cross-sectional path for the fluid flow. As shown in FIGS. 15A-15B, circular openings 272 are formed in the sheath 120. The openings 272 are positioned in a predetermined pattern in a non-obstructive fashion with the proximal split ring 274 and the distal rings 276, 278 of the snap-fit lock structure 280. Shown in FIGS. 15C-15D, the coupler 130 is formed with triangular openings 282 formed in the sheaths 120 in the non-obstructive fashion with the proximal ring 274 and distal rings 278, 276 of the snap-fit lock 280.

Although only circular and triangular openings 272, 282, respectively, are shown in FIGS. 15A-15D, other configurations of the cutouts in the plastic encapsulation are also contemplated in the subject structure to allow the passage of an injected contrast fluid through the cutouts.

Figure 16C:
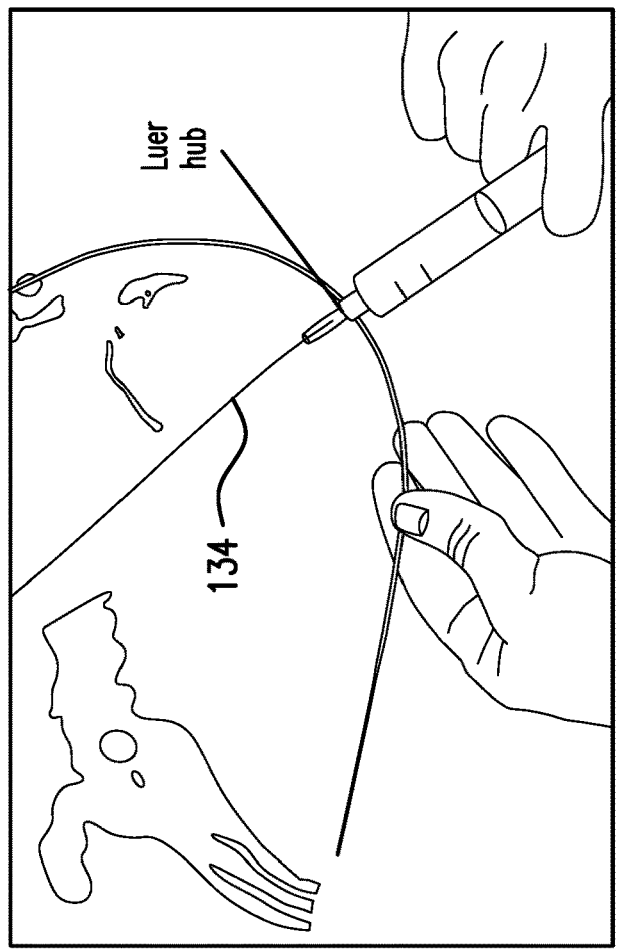
FIGS. 16A-16C are representative of the hypo-tube pusher flush lumen concept, with FIG. 16A depicting an isometric view of the proximal coupler of the outer catheter coupled with the pusher, FIG. 16B being a sectional isometric view of FIG. 16A depicting a flow channel in the pusher, and FIG. 16C showing a procedure of injecting a flushing fluid between the inner and outer catheters.
Figure 16A:
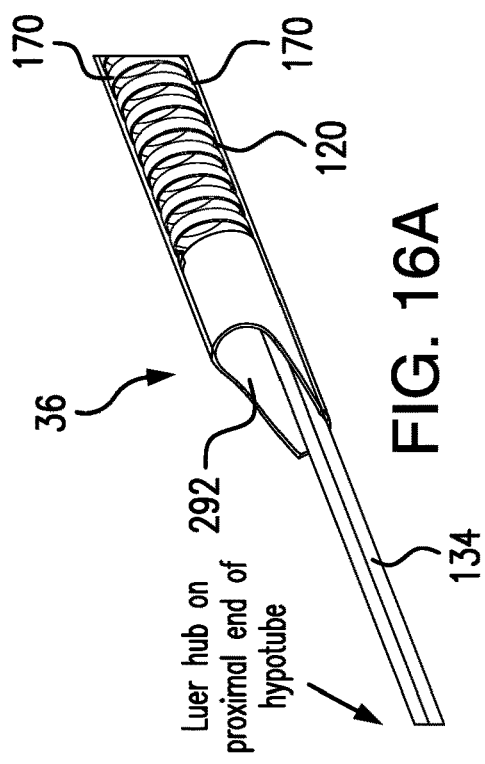
Figure 16B:
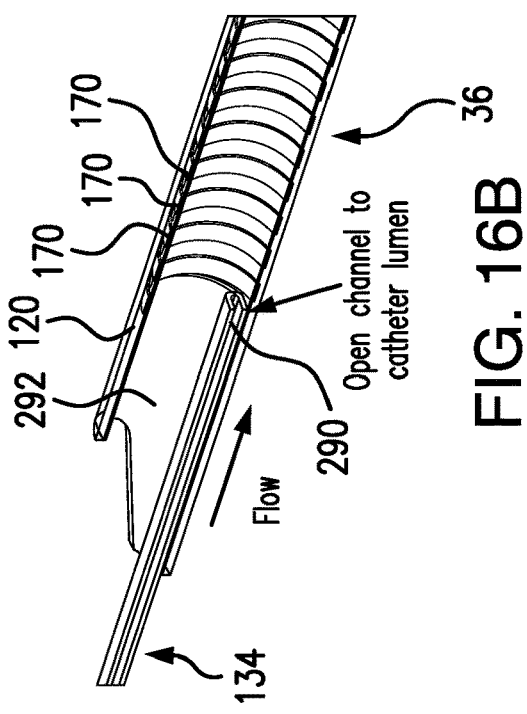

Referring to FIGS. 16A, 16B, and 16C, another embodiment of the proximal end of the outer catheter 36 is presented which is specifically designed as a potential solution to prevent an unwanted embolization situation when air is inadvertently entered with the fluid injected between the inner and outer catheters 34, 36. In order to prevent this, a flush lumen 290 is built into the pusher 134 via a flattened hypo-tube. A Luer hub is coupled to the proximal end of the hypo-tube (pusher 134) as shown in FIG. 16C, so that a surgeon can inject the fluid between the inner and outer catheters via the hypo-tube 134. When the fluid is entered into the outer catheter lumen 292 via the channel 290 in the hypo-tube 134, the entrance of air bubbles between the inner and outer catheters is prevented.

Further, referring to FIGS. 17A-17C, the interconnection unit 220 between the proximal coupler 130 presented in FIGS. 11A-11E, 12A-12C, 13A-13B, 14A-14B, and 15A-15D, includes the cooperating member 222 in the form of an annular round ring 252 (also referred to herein as a mid lock ring) formed on the outer surface 224 of the inner catheter 34. The stainless steel annular ring 252 is contoured with a full round surface which permits for smallest reversible engagement/disengagement from the need split-ring feature of the outer catheter coupler 130. The ring 252 as shown in FIG. 17C has a rounded contour on the outer surface 302 for smooth locking/unlocking action. The inner surface 304 of the ring 252 is also a smooth structure which is engaged with the outer surface 224 of the inner catheter 34.

FIG. 17A depicts the disengaged configuration of the inner catheter 34 relative to the outer catheter 36. FIG. 17B is representative of the lock engaged configuration when the inner catheter 34 is received and locked inside of the opening 210 at the proximal end of the sheath 120 so that the ring 252 is engaged in the snap-fit lock 306 formed by the distal solid ring 308 and the mid split ring 310. While in position, the proximal bevel split ring 312 encircles the inner catheter 34, and the ring 252 is locked in the snap-fit lock 306, thus engaging the inner and outer catheters for surgical manipulation as required by a surgical procedure.

During the longitudinal motion of the inner catheter 34 inside the outer catheter 36, while the ring 252 passes through the proximal bevel split ring 312 and the mid split ring 310, the arms of these rings are expanded from the original position to create a sufficient room for the ring 252 to pass. When in position, i.e., the ring 252 is received between the rings 308 and 310, the arms of the bevel split ring 312 and the split ring 310 return to their original closed position. The ring 252, being trapped between the rings 308, 310, is snap-fit locked therebetween, thus preventing the inner and outer catheters relative displacement.

Figure 18A:
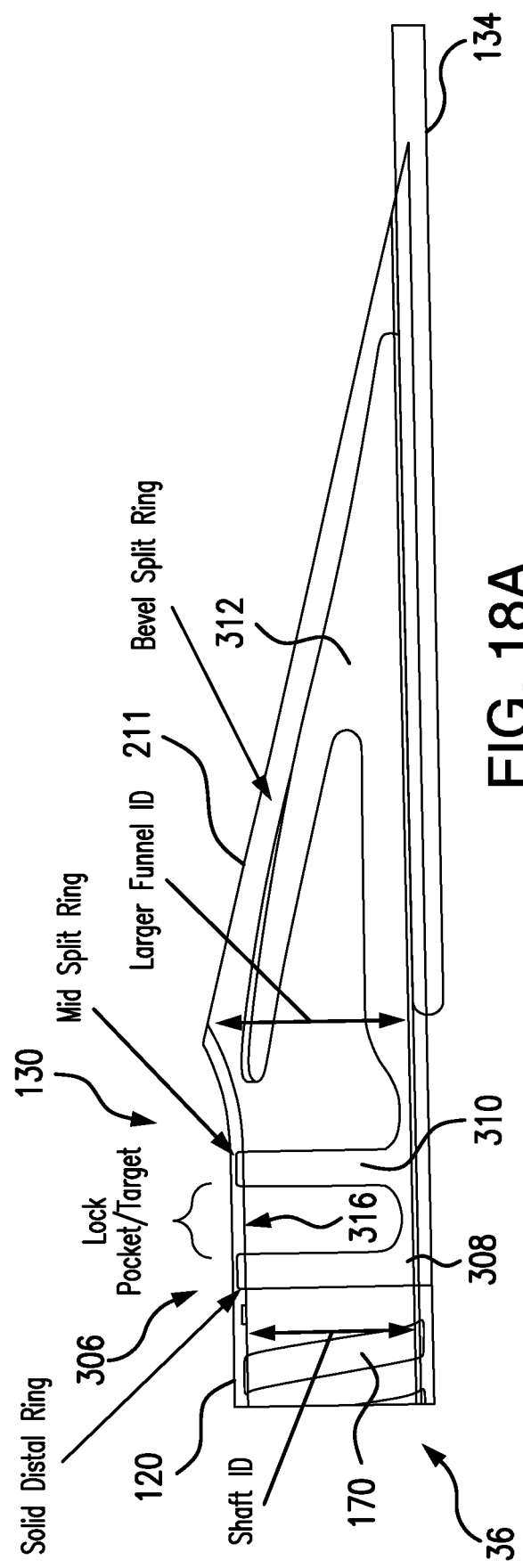
FIGS. 18A-18B detail the subject annular round ring lock mechanism shown in FIGS. 17A-17B. where
Figure 18B:
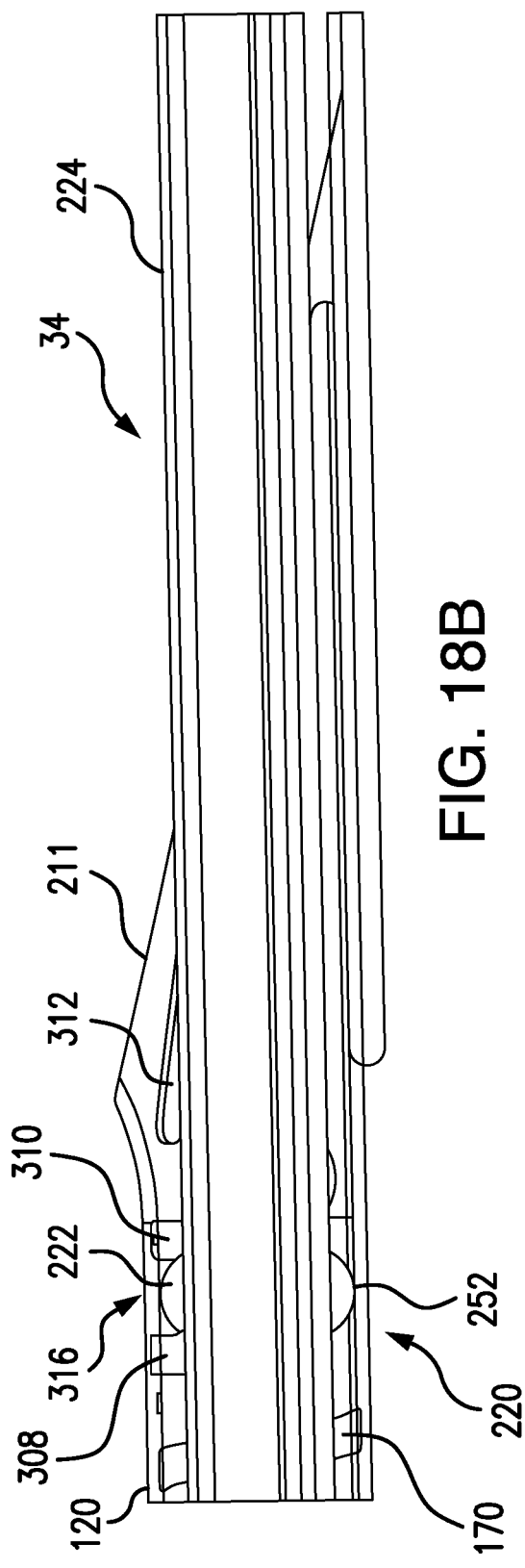

Referring to FIGS. 18A-18B, detailing the structure shown in FIGS. 17A-17C, it is shown that the section (pocket) 316 of the sheath 120 of the outer catheter 36 is not reinforced by the coils 170 and deflects when the mid shaft lock ring 252 is inserted between the solid distal ring 308 and the mid split ring 310 of the snap-fit lock 306. The deflected portion 316 of the sheath 120 between the rings 308 and 310 provides additional retention force to maintain the inner and outer catheters 34, 36 in locking engagement.

The stainless steel annular ring 252 may be attached to the outer surface 224 of the inner catheter shaft 34 via an adhesive. The lock ring geometry (full round surface) allows for a smooth reversible engagement/disengagement from the laser cut features of the outer catheter's coupler 130. The distal ring 308 of the snap-fit lock 306 prevents further distal motion of the inner catheter 34, while the mid-split ring 310 opens upon contact with the mid shaft lock ring 252 and provides the tactile snap. The proximal bevel split ring 312 allows for the funnel 211 to be opened to an internal diameter larger than the internal diameter of the rest of the shaft 120. It also allows for a smooth passage of the mid-shaft lock ring 252.

The interference between the unreinforced shaft pocket 316 and the mid shaft lock ring 252 provides retention of the inner catheter 34 to the outer catheter 36 until the user is ready to remove the inner catheter 34 from the outer catheter 36, thus disengaging the snap fit lock therebetween. The force required to disengage the lock mechanism can be tailored from 0.1 to 2.0 lbs.

Referring to FIG. 19A-19C, another alternative embodiment of the mid shaft lock is presented which includes a square annular ring (formed of a metallic or a polymeric material) 320. Unlike the ring 252, shown in FIGS. 17A-17C and 18B, the ring 320 has a square cross-section 321, shown in FIG. 19C. The square annular ring 320 is affixed to the outer surface 224 of the inner catheter 34 with a heat fused Pebax encapsulation 322. Alternatively, it may be glued to the inner catheter outer surface 224. As shown in FIG. 19B, when the inner catheter is in locked position, the square annular ring 320 snaps into the snap-fit lock 324 formed by the solid ring 326 and split ring 328, with the encapsulation 322 in contact with the internal surface 152 of the sheath 120 and with the ring 320 positioned between the rings 326 and 328.

Figure 20A:
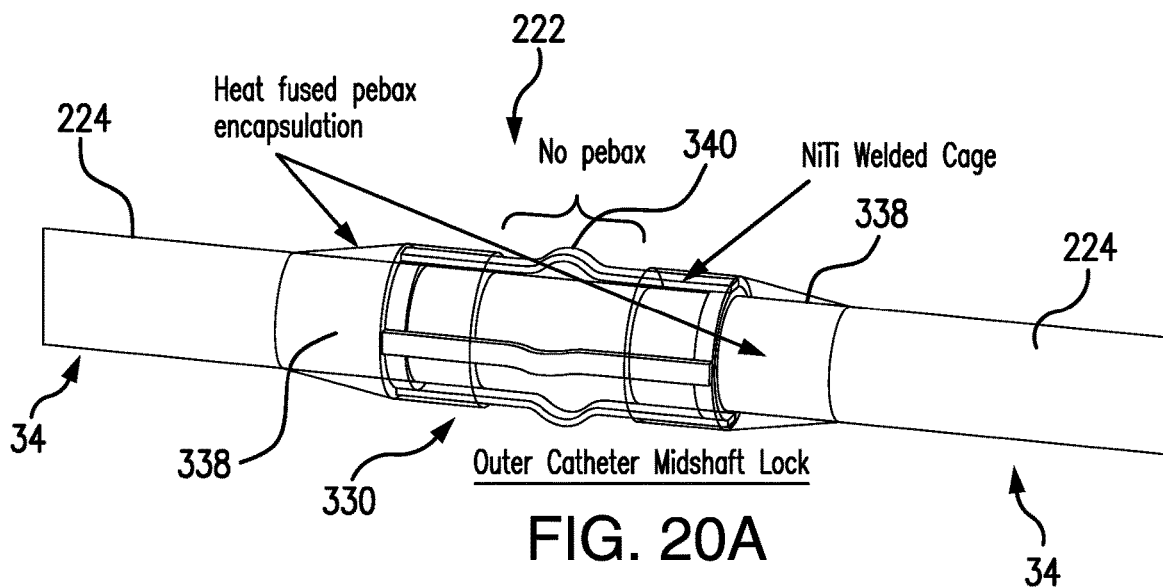
FIGS. 20A-20C depict the alternative "snap-fit cage" lock mechanism, with FIG. 20A showing the inner catheter with the welded cage lock, FIG. 20B showing the inner catheter's welded cage lock snapped in the outer catheter's proximal coupler, and FIG. 20C being an isometric view of the welded cage element.
Figure 20B:
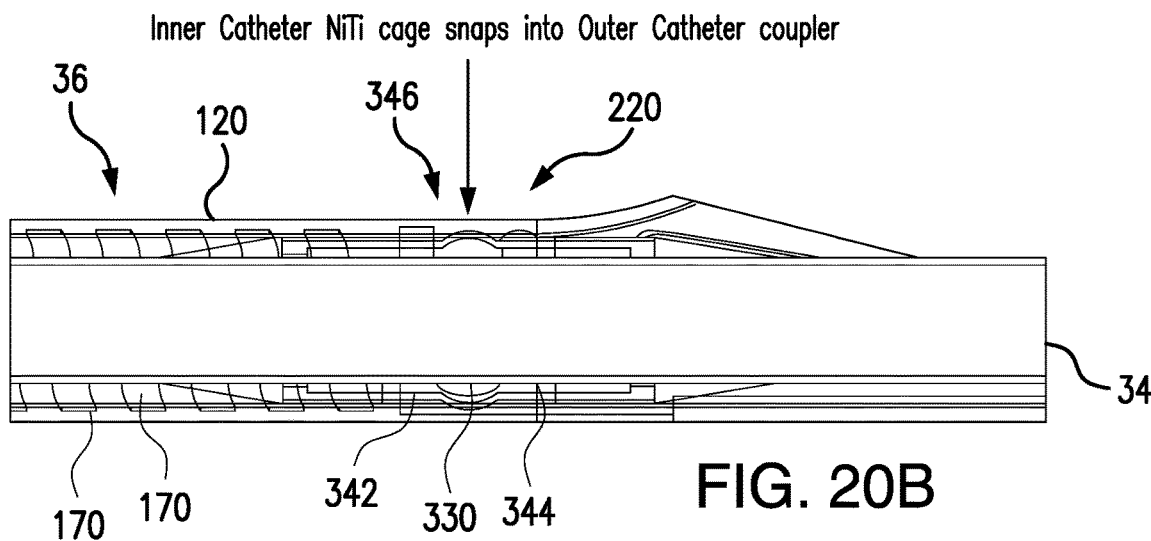
Figure 20C:
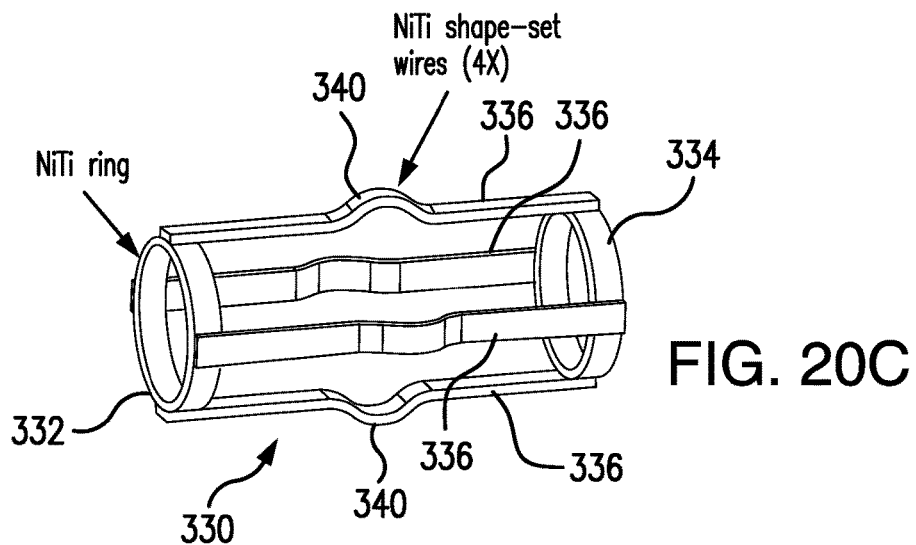

In a further alternative embodiment, shown in FIGS. 20A-20C, the mid-shaft lock mechanism 220 is formed with the cooperating member 222 in the form of a cage shaped structure 330 having two NiTi rings 332, 334 connected together through a number (for example, 4) of NiTi shape-set wires 336. As shown in FIG. 20A, the cage 330 is affixed to the outer surface 224 of the inner catheter 34 either by gluing or by heat fused Pebax encapsulation 338. Each of the wires 336 has an arcuated extending portion 340 which is left free from the encapsulation 338 as shown in FIGS. 20A and 20B.

As shown in FIG. 20B, for the locking configuration, the cage structure 330 snaps into the outer catheter's coupler 130. The un-encapsulated arcuated portion 340 of each wire 336 extends outside the encapsulation 338 and away from the wires 336 of the cage 330. When the cage 330 is received between the rings 342 and split ring 344 of the snap fit mechanism 346, the locking mechanism 346 is actuated, and the inner and outer catheters 34, 36 are engaged.

Referring further to FIG. 21, the proximal coupler 130 of the outer catheter 36 may include two locking slots 350, 352 which are formed by connected rings 354 and 356 with a connecting element 358.

Referring to FIGS. 17A-17C, 18A-18B, 19A-19B, 20A-20C, as well as 10A-10G, 11A-11C, 12A-12B, 13A-13B, 14A-14B, 15A-15D, and 21, when a surgeon linearly displaces the inner member 34 within the internal channel 122 of the proximal coupler 130, the snap-fit annular ring 252, 320, or the cage 330 enters the channel 122 between the arms of the proximal ring 240, 312, which are flexibly bent outwardly to permit forward motion of the inner catheter 34 (towards the distal tip 162). When the snap-fit annular ring 252, 320 or the cage 330 passes further through the mid split ring 244, 262, 268, 310, 328 of the snap-fit lock, the arms of the bevel proximal ring return to their original position, but the arms of the mid split ring are flexibly bent outwardly to allow the ring 252, 320 of the cage 330 to the position between the distal solid ring and the mid split ring. After the ring/cage 252, 320, 330 is snap-fit between the rings of the snap-fit locking mechanisms, the arms of the mid-split ring return to their original position.

In order to disengage the inner member 34 from the outer member 36, the surgeon pulls the inner member 34 from the internal channel of the proximal coupler 130. During the removal of the snap-fit annular ring/cage 252, 320, 330 from the channel, the pulling action causes the arms of the mid-split ring to bend outwardly to permit the passage of the snap-fit annular ring/cage 252, 320, 330 therebetween, thus freeing the inner catheter 34 from the proximal coupler 130 of the outer catheter 36.

Returning to FIG. 3D, the inflation lumen distal shaft 66 at the middle section 42 of the subject guide catheter/pre-dilatation extension system 10 may be manufactured with braid reinforcement structure 260. The braid reinforcement member 260 creates a somewhat flexible tubing connected to the cooperating mechanism 222 of the interconnection unit 220 of the inner member 34. The RX (Rapid Exchange) port 94 for passing the guide wire 12 may be formed through the wall of the braid reinforced inflation lumen distal shaft 66.

The braid reinforcement structure 260 may be configured with metallic patterns or wires within the braid reinforced inflation lumen distal shaft 66 to prevent kinking, which would give the shaft 66 a longitudinal stiffness. The metal braid 260 may be embedded in the braid reinforced shaft 66 to add increased flexibility thereto required for retraction of the inner member 34 relative to the outer delivery sheath 120 during the procedure.

A flat wire helical coil (made, for example, from a shape memory alloy, such as Nitinol) with a wire thickness of approximately 1 mil to 3 mils may be embedded in the braid 260. This coil may be formed with a very thin coating of plastic placed onto its inner and outer surfaces, which facilitates the reduction of the wall thickness of the inflation lumen distal shaft 66 to less than 7 mils and preferably to approximately 5 mils.

The principles of reinforcing the tubular members by the catheter shaft coil reinforcement 170 in a form of a flat wire helical coil 262 or forming the tubular members from the flat wire helical coil may be applied in the subject guide catheter extension/pre-dilatation system 10 to the outer delivery sheath 120 (as shown in FIGS. 7, 8B, 9A-9D, 10A, 11C, 12B-12C, 13A-13B, 14B, 15A-15C, 16A-16B, 17A-17B, 18A-18B, 19B, 20B, and 21, as well as to the micro-catheter 46 (as shown in FIGS. 2A-2B, 5A, 22, and 24A-24B). In the outer delivery sheath 120 and/or the micro-catheter 46, such flat wire helical coil may be embedded in predetermined positions along the length of the walls thereof, for example, at the proximal and or distal ends.

Alternatively, the entire length of the outer delivery sheath 120 and/or micro-catheter 46 may be formed with the flat wire helical coil. The pitch between the coils may be adjusted to provide the flexibility gradient along the length of the tubular member (sheath 120 and or micro-catheter 46) increasing towards the distal end thereof to facilitate atraumatic operation.

Referring to FIGS. 22A-22B and 23A-23C, rather than utilizing a standard over-the-wire (OTW) guidewire lumen, a monorail Rapid Exchange (RX) design of the inner catheter 34' may be implemented to allow for the use of short guidewires. In the embodiment shown in FIGS. 22A and 22B, which represent the isometric view of the subject coil reinforced inner member shaft 400 and the side view taken along lines A-A thereof, the distal section 40' of the inner member 34' includes a tapered element 402 attached to the outer surface 224 of the inner member 34. The outer shaft 400 of the inner member 34' is a coil reinforced with coil reinforcement structure 404 extending from the distal tip 406 to the RX entry port 94 shown in FIGS. 2A-2C and 3C-3D. The distal tip 406 is a tapered soft tip which, along with the tapered element 402, interfaces with inner surface of the outer catheter 36 when the inner catheter 34' is charged in the outer catheter 36, as required by the surgical procedure.

The distal section 40' contains a concentric guidewire lumen 408, which communicates with the RX entry port at the proximal end of the inner catheter 34 (shown in FIGS. 2A-2C, and 3C-3D).

Figure 23A:
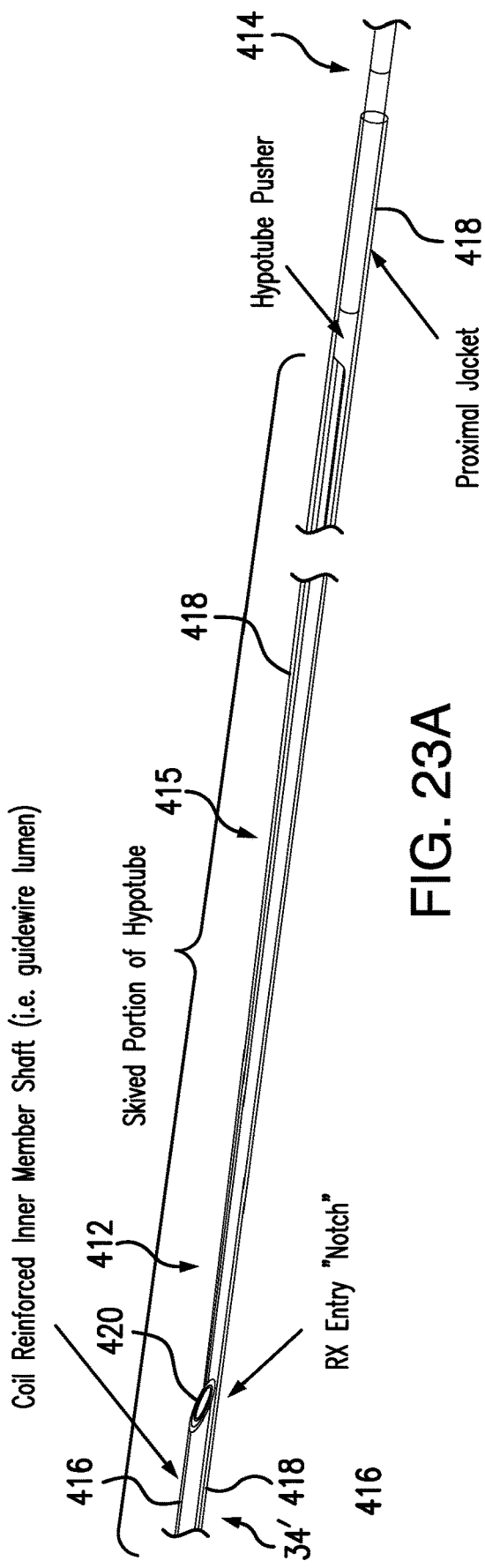

Shown in FIGS. 23A-23C, the proximal end 412 of the monorail micro-catheter embodiment shown in FIGS. 22A-22B utilizes a skived hypo-tube pusher 414. The proximal end 412 of the coil reinforced inner member shaft 416 and the hypo-tube pusher 414 are encapsulated in the proximal outer jacket 418, which extends as a tube along the proximal end 412 of the monorail micro-catheter embodiment of the inner member 34', from (and including) the coil reinforced inner member shaft 416 (which serves as a guidewire lumen) 408 shown in FIGS. 22A-22B and the hypo-tube pusher 414.

The embodiment depicted in FIGS. 23A-23B features an RX guidewire "notch" termination/entry 420 which is fabricated by piercing the proximal outer jacket 418. Subsequently, the coil reinforced inner member shaft 416 is inserted into the proximal outer jacket tube 418 via the RX entry "notch" 420. The skived hypo-tube 415 is further inserted into the proximal outer jacket tube 418 via its lumen 422, and the polymers of the coil reinforced inner member shaft 416 and the proximal outer jacket tube 418 are fused together to connect the inner member shaft 416 and the pusher 414 and, thus, to form the proximal end 412 of the monorail micro catheter inner member 34'.

For convenience of the surgeon, the pushing/pulling element 134 of the outer catheter 36 may be colored (color coated), as shown in FIG. 11A, to have a distinguished color to differentiate it from other elements of the system, such as the pushing/pulling element of the inner catheter 34, as well as from the usual gray or silver color of a coronary guidewire used to deliver the device or a stent delivery system. Alternatively, the proximal outer jacket 418 of the pushing-pulling element 414 may be color coated to distinguish its color from the colors of other elements in the subject system.

Referring further to FIGS. 24A-24B, representative of an additional coil reinforced balloon catheter embodiment 500 of the inner catheter, the structure combines the reinforced shaft properties of the micro-catheter 46 with that of the dilatation balloon 44 with the following attributes:

a. Coil reinforced shaft 502 provides an additional kink resistance and pushability while still maintaining flexibility for navigating tortuous vasculature; and b. The structure's longer distal tip 504 contains low profile, tapered soft tip to facilitate crossing the stenosis and tight lesions.

As shown in FIGS. 24A-24B, the distal section 504 of the subject structure 500 includes the inner member shaft 500 reinforced with the coil reinforcement structure 506 which extends the length of the inner member's shaft 500. The distal tapered element 508 is positioned on the inner member shaft 500 and extends between the ends 510 and 512 in encircling relationship with the inner member shaft 500. The distal tapered soft tip 514 may be in the form of the micro catheter 46 which is positioned at the end of the coil reinforced shaft 500.

Similar to the embodiment presented in FIGS. 22A-22B, the balloon member 44 is positioned on the inner member shaft 500 with the radio opaque markers 264 and 266 positioned on the inner member shaft 500 within the balloon member 44. At its proximal end 516, the balloon member 44 interferes with the outer tip 164 of the proximal tapered element 178 of the outer member sheath 120. At the distal end 518, the balloon member 44 snugly embraces the shaft 500.

Returning to FIGS. 1-24B, in operation, for performing the cardiac procedure, and specifically the pre-dilatation routine, a proximal end of the coronary guidewire 12 is entered into the RX port 94 formed in the inflation lumen distal shaft 66, and is extended through the inner channel (GW lumen 96) of the inner member 34 towards and beyond the outermost distal end 52 of the micro-catheter 46. Subsequent thereto, the guide catheter 14 is advanced into the blood vessel 16 of interest.

Subsequently, the outer delivery sheath 120 of the outer member 36 locked with the inner member 34 therewithin, are placed first with the micro-catheter 46 in the internal channel 48 of the guide catheter 14, and both inner and outer members 34, 36 as a single unit, are integrally advanced within the guide catheter 14 towards the treatment site 22. The outer member's sheath 120 and the inner member 34 may be integrally displaced by pushing the outer member pusher 134. This action causes the micro-catheter 46 of the inner member 34 to slide along the GW 12 along with the outer member 36 until they extend beyond the distal end 50 of the guide catheter 14, and reach the lesion site 92. In this step of the procedure, the balloon member 44 is in its deflated configuration.

The guidewire 12 which extends beyond the distal end 50 of the guide catheter 14, serves as a guide along which the micro-catheter 46 (with the deflated balloon 44 attached to the distal tip 162) slides towards the treatment site 26.

Subsequently, the balloon member 44 (which is positioned at the treatment site 22) is inflated by the balloon inflation system 62 connected to the inflation hub 56 through the inflation lumen formed by the inflation lumen distal shaft 66 and the inflation lumen hypotube 64 in order to compress the plaque and to widen the blood passage inside the blood vessel 16.

Subsequently, once the lesion has been dilated, the balloon 44 is deflated, and the outer delivery sheath 120 may be advanced across the lesion 22 either as an integral unit with the inner member 34 (in the engaged mode of operation), and the inner member may be subsequently disengaged (unlocked) from the outer delivery sheath 120 and removed from the sheath 120.

Alternatively, the inner member 34 may be disengaged and withdrawn from the sheath 120 directly after the lesion dilatation, while the outer member 36 is advanced across the lesion 22.

The sheath 120 may be left in place (directly after the dilatation of the lesion) proximal to the treatment site.

Subsequent to pulling the inner member 34, the stent can be delivered to the site 22. The stent, in its closed configuration, may be introduced into the blood vessel 16 inside the sheath 120. When in place, the stent supporting balloon (not shown) may be expanded, thus opening the stent. Subsequently, the outer delivery sheath 120 is removed, leaving the opened stent in the blood vessel 16.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. An intravascular delivery system comprising:
    an outer member defining a sheath lumen, wherein the outer member comprises an outer member proximal end and an outer member distal end, wherein the outer member proximal end comprises an elongate mouth, wherein the elongate mouth extends along a diagonal,
    wherein the outer member further comprises a proximal split ring positioned near the elongate mouth, wherein the proximal split ring extends along the diagonal of the elongate mouth,
    wherein the outer member comprises a distal split ring and a solid distal ring, wherein the distal split ring is positioned between the proximal split ring and the solid distal ring, wherein a space is formed between the distal split ring and the solid distal ring,
    wherein the outer member further comprises a plurality of openings, wherein the plurality of openings are positioned between the proximal split ring and the distal split ring; and
    an inner member, wherein the inner member is configured to be disposed at least partially within the sheath lumen of the outer member, wherein the inner member comprises a delivery catheter configured to extend from the outer member distal end,
    wherein the inner member comprises an engagement member, wherein the engagement member is configured to be guided by the elongate mouth and the proximal split ring into the sheath lumen of the outer member and toward the distal split ring,
    wherein the engagement member is configured to expand the distal split ring as the engagement member passes through the distal split ring, wherein the engagement member is configured to be disposed in the space formed between the distal split ring and the solid distal ring, wherein the inner member and the outer member are engaged for a controllable common displacement when the engagement member is disposed in the space formed between the distal split ring and the solid distal ring.

2. The intravascular delivery system of claim 1, wherein the plurality of openings are circular.

3. The intravascular delivery system of claim 1, wherein the plurality of openings are configured to improve a contrast infusion flow rate by providing an additional open cross-sectional path for fluid flow.

4. The intravascular delivery system of claim 1, wherein the plurality of openings are positioned in a predetermined pattern.

5. The intravascular delivery system of claim 1, wherein the plurality of openings are positioned in a non-obstructive manner with the distal split ring and the solid distal ring.

6. The intravascular delivery system of claim 1, wherein the plurality of openings are positioned in a non-obstructive manner with the proximal split ring.

7. The intravascular delivery system of claim 1, wherein the plurality of openings are triangular.

8. The intravascular delivery system of claim 1, wherein the plurality of openings are cutouts to allow the passage of an injected contrast fluid.

9. The intravascular delivery system of claim 1, wherein the plurality of openings comprise two openings that are diametrically opposed.

10. The intravascular delivery system of claim 1, wherein the plurality of openings comprise two openings that are aligned.

11. The intravascular delivery system of claim 1, wherein the outer member comprises a plastic encapsulation.

12. The intravascular delivery system of claim 1, wherein the outer member comprises a lubricious liner.

13. The intravascular delivery system of claim 1, wherein the proximal split ring comprises a distal edge, wherein at least one opening of the plurality of openings is proximal to the distal edge of the proximal split ring.

14. The intravascular delivery system of claim 1, wherein the proximal split ring comprises a distal edge, wherein at least a portion of an opening of the plurality of openings is proximal to the distal edge of the proximal split ring.

15. The intravascular delivery system of claim 1, wherein the inner member and the outer member are configured to be disengaged for retraction of the inner member from the outer member.

16. The intravascular delivery system of claim 1, wherein the distal split ring is configured such that a pulling action causes arms of the distal split ring to bend outwardly to permit the passage of the engagement member therebetween.

17. The intravascular delivery system of claim 1, wherein the outer member comprises an outer cylindrical surface.

18. The intravascular delivery system of claim 1, wherein the elongate mouth comprises a flared opening.

19. The intravascular delivery system of claim 1, wherein the engagement member comprises an annular ring coupled to the inner member.

20. The intravascular delivery system of claim 1, wherein the engagement member comprises an annular ring comprising a smooth rounded surface.

* * * * *